United States Patent
Sun et al.

(10) Patent No.: US 9,889,093 B2
(45) Date of Patent: Feb. 13, 2018

(54) APPLICATION OF ANDROGRAPHOLIDE IN THE PREPARATION OF A PHARMACEUTICAL FOR TREATMENT OF INFLAMMATORY BOWEL DISEASE, ANDROGRAPHOLIDE ENTERIC TARGETING MICROPELLET, AND METHOD FOR PREPARATION THEREOF

(71) Applicant: TASLY PHARMACEUTICAL GROUP CO., LTD., Tianjin (CN)

(72) Inventors: Henry Sun, Tianjin (CN); Xiaohui Ma, Tianjin (CN); Zhixin Guo, Tianjin (CN); Sen Lin, Tianjin (CN); Genbei Wang, Tianjin (CN); Lulu Yan, Tianjin (CN); Lihua Zhang, Tianjin (CN); Shuiping Zhou, Tianjin (CN); Shunnan Zhang, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 0 days.

(21) Appl. No.: 14/910,173

(22) PCT Filed: Aug. 6, 2014

(86) PCT No.: PCT/CN2014/083810
§ 371 (c)(1),
(2) Date: Feb. 4, 2016

(87) PCT Pub. No.: WO2015/018344
PCT Pub. Date: Feb. 12, 2015

(65) Prior Publication Data
US 2016/0175253 A1    Jun. 23, 2016

(30) Foreign Application Priority Data

Aug. 6, 2013   (CN) .......................... 2013 1 0338444

(51) Int. Cl.
| | | |
|---|---|---|
| *A61K 9/16* | (2006.01) | |
| *A61K 31/365* | (2006.01) | |
| *A61K 9/50* | (2006.01) | |
| *B01J 2/00* | (2006.01) | |

(52) U.S. Cl.
CPC .......... *A61K 9/1682* (2013.01); *A61K 9/1635* (2013.01); *A61K 9/1676* (2013.01); *A61K 9/5026* (2013.01); *A61K 9/5078* (2013.01); *A61K 31/365* (2013.01); *B01J 2/006* (2013.01)

(58) Field of Classification Search
CPC .. A61K 9/1682; A61K 31/365; A61K 9/5026; A61K 9/5078; A61K 9/1676; A61K 9/1635; B01J 2/006
See application file for complete search history.

(56) References Cited

U.S. PATENT DOCUMENTS

2012/0141584 A1*  6/2012  Chauhan .............. A61K 9/2072
                                                              424/457

FOREIGN PATENT DOCUMENTS

| CN | 101422494 A |   | 5/2009 | |
|---|---|---|---|---|
| CN | 102614133   | * | 8/2012 | |
| CN | 102614133 A |   | 8/2012 | |
| CN | 10307843    | * | 5/2013 | |
| CN | 103070843   | * | 5/2013 | ............. A61K 47/32 |
| CN | 103070843 A |   | 5/2013 | |

OTHER PUBLICATIONS

Soravoot Rujivipat & Roland Bodmeier, Moisture Plasticization for Enteric Eudragit L30D-55-Coated Pellets Prior to Compression into Tablets, 81 Eur. J Pharma. Biopharma. 223 (2012).*
Laila Fatima, et al, Multiparticulate Formulation Approach to Colon Specific Drug Delivery: Current Perspectives, 9 J Pharm. Pharmaceut. Sci. 327 (2006).*

* cited by examiner

*Primary Examiner* — Sean M Basquill
(74) *Attorney, Agent, or Firm* — Dilworth & Barrese, LLP

(57) ABSTRACT

The present invention relates to an andrographolide enteric targeting micropellet and a method for preparation thereof; furthermore, the present invention also relates to uses of andrographolide and andrographolide enteric targeting micropellets in preparation of a pharmaceutical for treatment of inflammatory bowel disease.

16 Claims, 5 Drawing Sheets

Figure 2:
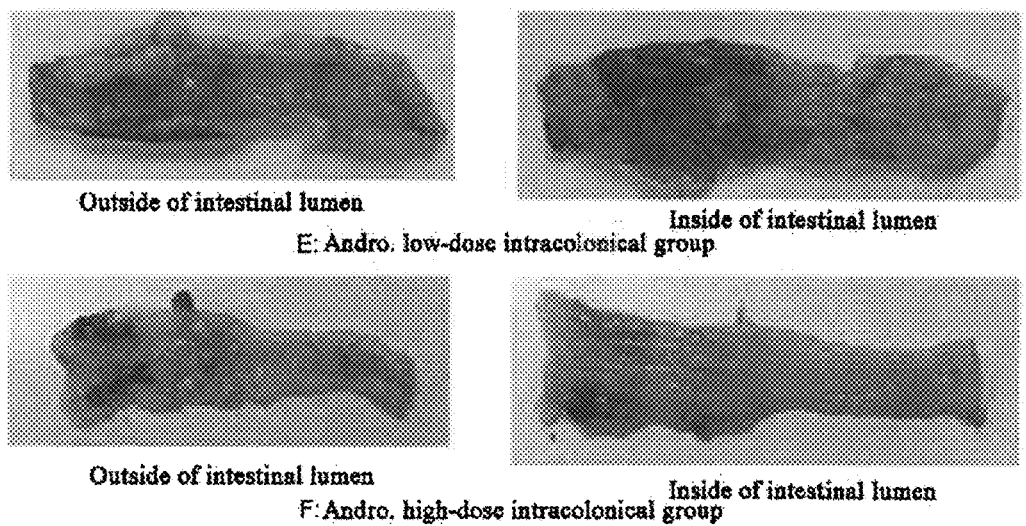

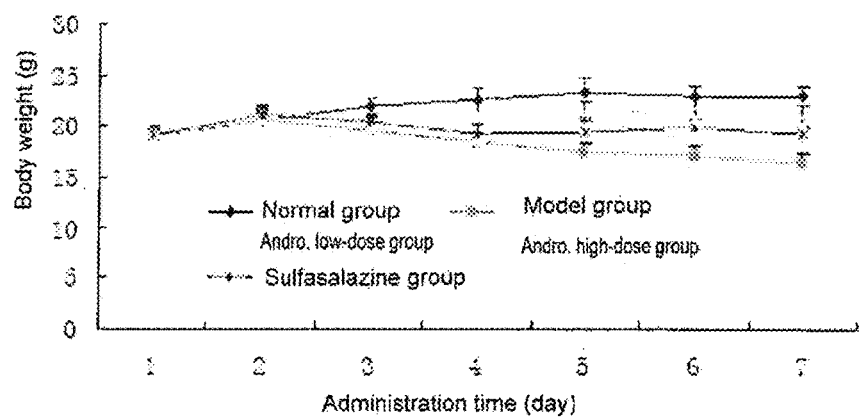
Fig. 1
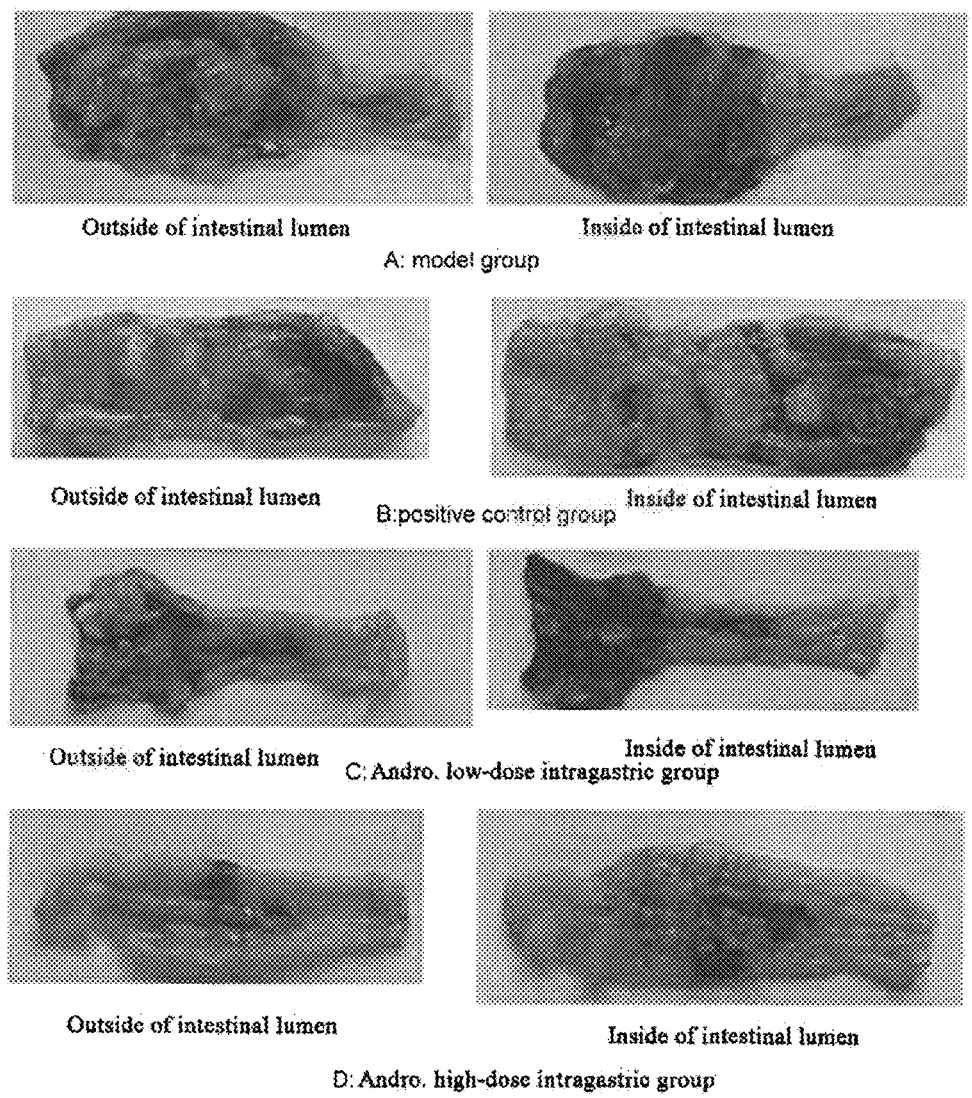

APPLICATION OF ANDROGRAPHOLIDE IN THE PREPARATION OF A PHARMACEUTICAL FOR TREATMENT OF INFLAMMATORY BOWEL DISEASE, ANDROGRAPHOLIDE ENTERIC TARGETING MICROPELLET, AND METHOD FOR PREPARATION THEREOF

FIELD OF THE INVENTION

The present invention relates to the field of medicine. More specifically, the invention relates to an andrographolide enteric targeting micropellet and a method for preparation thereof. Also, the present invention relates to a use of andrographolide and andrographolide enteric targeting micropellet in preparation of a medicine for treatment of inflammatory bowel disease.

BACKGROUND OF THE INVENTION

Andrographolide ($C_{20}H_{30}O_5$) is the diterpene lactone compound extracted from the Acanthaceae plant of *Andrographis Paniculata*. It is one of the main effective components in the *Andrographis Paniculata Nees* which is crowned as the natural antibiotic because of its effects of anti-pathogenic microorganism, antipyresis, anti-inflammation, improving body immune, protecting liver by normalizing functioning of the gallbladder and anti-tumor etc. The andrographolide belongs to the diterpene lactone compound. Being an herbal extract, it has advantages of less side effects, better anti-inflammation and extensive source with a competitive price.

Inflammatory bowel disease (IBD) is a recurrent chronic inflammatory disease in the intestinal tract, mainly includes ulcerative colitis (UC) and Crohn's disease (CD). Their definite cause and pathogenesis have not been elucidated and therefore it is still lack of effective treatment methods in clinic. The clinical manifestations of UC include: the intestinal tract injury, most of which firstly appeared in distal colon and sigmoid colon; mainly the left abdomen sustained vague pain or dull pain, which may be relieved after diarrhea; the myxoid-like and pus-blood-like stool accompanied with tenesmus. The clinical manifestations of CD include: mostly abdomen pain; the left abdomen colic pain or spastic sharp pain characterized by paroxysmal occurrence and colic pain mostly occurs post meal; the myxoid-like and watery stool accompanied with constipation alternative with diarrhea. A series of diseases may be more likely to be found in CD than in UC, such as intestinal stenosis, intestinal obstruction, intestinal fistula, intestinal polyp and even carcinogenesis.

Crohn's disease (CD) is identified as one of the IBD. Usually, the symptoms of inflammation, congestion or swollen lymph may occur in the colon, small intestine or stomach of the patient. The main difference between the CD and UC lies in inflammation position and inflammation itself. The Crohn's disease may affect any segment of digestive system, e.g. small intestine, colon, stomach and esophagus, which is common in terminal ileum and adjacent colon segment and right-half colon. UC, however, just occurs in colon and rectum, which is common in rectum and sigmoid colon. Microscopically, the Crohn's disease may affect whole inner wall of bowel, while UC is restricted to mucosa.

Crohn's disease is a chronic and recurrent disease. Effectively therapeutical drugs have not yet been developed for its unknown cause. By now, drugs used for treating Crohn's disease mainly include glucocorticoid, salicylic acid formulations, immunosuppressive agents, antibiotics, methotrexate and biological agents (e.g. infliximab). Although these drugs are proven to be able to change the natural process of disease, they cannot completely alleviate the conditions of disease and decrease the incidence of complications. Moreover, the known western medicines such as glucocorticoid and immunosuppressive agents often cause obvious adverse reaction, and long-term administration will likely result in damage to the body. Hence, we need to develop a new medicine and its formulation thereof for treatment of Crohn's disease.

On the other hand, the colon drug delivery has been regarded as a difficult issue in R&D for a long time, which is determined by colon's own physiological characteristics. It is well-known that the colon is located in the bottom half of the digestive tract, that drugs are very difficult to reach the colon when administrated orally and that enema administration is both inconvenient and painful. As a result of this, the colon targeting preparation technique emerged. Oral colon-specific drug delivery system (OCSDDS) refers to a site-specific drug delivery system, which makes the drug pass through the top half of the digestive tract of stomach and duodenum without any release of the drug, and the medicine is not released until being transferred to ileocecum to demonstrate local or systematic therapeutic effects by a drug delivery technique. The common-used OCSDDS techniques are divided into the pH-dependent type and the enzyme-degraded type.

The pH-dependent OCSDDS is to achieve the colon specific delivery by utilizing the different pH value of each part in human gastrointestinal tract. Usually, the gastric pH value of healthy people is lowest at 1~3, the duodenum at 4~6, the jejunum at 6~7, the ileum at 7~7.5 and the colon at 7~8.

Now, the common-used enteric-coating materials have different pH values at which to dissolve. The first type began to dissolve at pH value≥5.5, the second at ≥6.0 and the third at ≥7.0. Up to now, the drug is wrapped by using the third enteric polymer material to coat in the pH-dependent enteric-targeting preparation. It may be achieved that the drug does not release through the top half of the gastrointestinal tract until being transferred to the ileocecum. All Chinese patents (CN1981743, CN101209246, CN103315959) are involved in this technique. As shown in clinical studies, however, gastrointestinal pH values among different individuals are far away from each other. There is a gap between IBD patients and healthy people, and the colon pH value in colitis patients is lower than that in healthy people. As a result, when using this kind of polymer alone, the drug will not be released in vitro and expelled with stool.

As for the enzyme-degraded oral colon-specific delivery of andrographolide, the prior arts include the following steps: coating blank pellet core with the andrographolide to give a drug-loading micropellet; and wrapping said micropellet with a water-insoluble polymer in which mono-saccharides pore-forming agents are contained. The membrane of said polymer does not release in stomach and small intestine until reaching colon. The monosaccharide in the membrane is degraded by colon enzymes to form the pore in the membrane, thereby the drug is gradually dissolved and released. Although this technique has overcome defects of difference among individuals in the pH-dependent OCSDDS, there are some problems. Because the monosaccharide, e.g. Guar gum is dissolved in water and the drug will be soon released from pores formed by dissolution of monosaccharide after entering the body, it is difficult to ensure that effective amount of drug reaches the colon. In addition, the monosaccharide molecule is structurally rigid. Once being embedded among the polymer chains, it will not only affect the extensibility of polymer chain, but also destroy the integrity of polymer membrane, which will make the coating membrane crisped and easily broken. Hence, the risk is increased that the membrane may be early broken during transportation or by gastrointestinal peristalsis. As a result of this, developing new preparations of andrographolide is still needed for treating the IBD.

CONTENT OF THE INVENTION

In the first aspect, the objective of the present invention is to provide a new use of andrographolide, particularly, to a use of andrographolide in preparation of medicine for treating IBD. Wherein, said IBD includes UC and Crohn's disease.

On the other hand, the objective of the present invention is to provide a new pH-dependent enteric targeting preparation. That is to say, two types of pH-dependent polymers are jointly used to achieve the purpose of targeting release in vitro with different pH values of the intestinal tract. In particular, the present invention relates to an andrographolide enteric targeting micropellet. Said micropellet is used for better treating IBD, for example UC and Crohn's disease. Also, the present invention relates to a method for preparing said pH-dependent enteric targeting preparation.

Preferably, the present invention relates to the technical solutions as follows:

1. An andrographolide enteric targeting micropellet, characterized in that, said andrographolide enteric targeting micropellet is composed of a blank pellet core, a drug layer and an enteric coating layer, wherein said drug layer contains the andrographolide, a polymer A dissolved under a condition of pH≥7.0 and an excipient; the ratio of the andrographolide and the polymer A is 1:2~1:0.2 by weight; a weight gain of the drug layer is 20 wt %~100 wt %, preferably 30 wt %~80 wt %; said enteric coating layer contains the polymer B dissolved under a condition of pH≥5.5 and an excipient; a weight gain of the enteric coating layer is 5 wt %~30 wt %, preferably 8 wt %~20 wt %, most preferably 10 wt %~18 wt %.

2. The micropellet according to the $1^{st}$ paragraph, wherein,
said excipients contained in the drug layer include plasticizers, anti-sticking agents, pigments, hydrophilic polymers and surfactants; and
said excipients contained in the enteric coating layer include plasticizers and anti-sticking agents, preferably said excipients further include hydrophilic polymers and pigments.

3. The micropellet according to the $1^{st}$ paragraph, wherein said polymer A is a copolymer of methacrylic acid and methyl methacrylate, and said polymer B is a copolymer of methacrylic acid and ethyl acrylate.

4. The micropellet according to the $1^{st}$ paragraph, wherein said polymer A is the copolymer of methacrylic acid and methyl methacrylate in a ratio of 1:2, and/or said polymer B the copolymer of methacrylic acid and ethyl acrylate in a ratio of 1:1.

5. The micropellet according to the $2^{nd}$ paragraph, wherein said plasticizer is one or more selected from the group consisting of triethyl citrate, dibutyl sebacate, propanediol and PEG, the amount of the plasticizer is 10 wt %~70 wt % of the polymer A, preferably 10 wt %~20 wt % of the polymer A; said anti-sticking agent is talc powder, the amount of the anti-sticking agent is 25 wt %~100 wt % of the polymer A, preferably 30 wt %~50 wt % of the polymer A; or said anti-sticking agent is glyceryl monostearate, the amount of the anti-sticking agent is 2 wt %~20 wt % of the polymer A, preferably 5 wt %~10 wt % of the polymer A.

6. The micropellet according to the $1^{st}$ paragraph, wherein the diameter of said blank pellet core is 200~600 μm, preferably 300~500 μm, and the amount of the blank pellet core is 10 wt %~70 wt % of the formulation, preferably 20 wt %~60 wt % of the formulation.

7. The micropellet according to the $2^{nd}$ paragraph, wherein said ingredients are presented in proportion by weight parts:the blank pellet core:the andrographolide:the polymer A:the plasticizer:the anti-sticking agent:the surfactant=200:(10-100):(10-100):(1-15):(1-30):(0-3), preferably 200:(15-66):(13-74):(2-13.5):(3-27):(0-1.32), most preferably 200:(20-50):(30-60):(5-10):(5-20):(0.5-1.2).

8. A preparation method according to any one of the micropellets of the $1^{st}$~$7^{th}$ paragraphs, comprising the following steps:
(1) Applying the Drug to the Blank Pellet Cores
a). dispersing the polymer A into a pharmaceutical solvent to allow it dissolve fully by mechanical stirring to obtain a polymer A solution; adding the excipient into the polymer A solution, and then adding the andrographolide, well stirring to give a polymer A coating solution; and
b). weighing the blank pellet cores and charging into a fluidized bed; adjusting an air flow to make the blank pellet cores in a well fluidized state; starting a heating device until a temperature of the blank pellet cores material reaches a preset value, and starting a peristaltic pump to make the polymer A coating solution atomized through a spray gun and uniformly dispersed on the surface of said blank pellet cores to obtain drug-loading micropellets;
(2) Preparation of the Enteric Coating Layer
a). dispersing the polymer B into a pharmaceutical organic solvent or water to allow it dissolve fully by mechanical stirring to obtain a polymer B solution; adding the excipient into the polymer B solution, well stirring to give a polymer B coating solution; and
b). charging said drug-loading micropellets into a bottom-spray device of the fluidized bed and coating by utilizing a fluidized bed device, and the polymer B coating solution is uniformly spread to form the enteric coating layer; the weight gain of the enteric coating layer is 5 wt %~30 wt %.

9. The preparation method according to the $8^{th}$ paragraph, comprising the following steps:
(1) Applying the Drug to the Blank Pellet Cores
a). dispersing the polymer A into the pharmaceutical ethanol to make the content of the polymer A at 5 wt %, fully dissolving the polymer A by mechanical stirring to obtain the polymer A solution; continuing to stir uniformly, adding the plasticizer, the anti-sticking agent and the surfactant of sodium dodecyl sulfate as the excipients into the polymer A solution and then adding the andrographolide, well stirring to give the polymer A coating solution; and
b). weighing the blank sucrose pellet cores in a diameter of 200~600 μm and charging into the fluidized bed; adjusting the air flow to make the pellet cores in a well fluidized state; starting a heating device and maintaining the temperature of the blank pellet cores material at 25-35° C., and starting a peristaltic pump until the temperature of the blank pellet cores material reaches a preset value to make the polymer A coating solution atomized through a spray gun and uniformly dispersed on the surface of said blank pellet cores to obtain drug-loading micropellets;

(2) Preparation of the Enteric Coating Layer a). dispersing the polymer B into the pharmaceutical ethanol to allow it dissolve fully by high-speed shearing mechanical stirring; adding the plasticizer and the anti-sticking agent as the excipient into the polymer B solution, well stirring to give the polymer B coating solution; and b). charging said drug-loading micropellets into a bottom-spray device of the fluidized bed and coating by utilizing a fluidized bed device, and the polymer B coating solution is uniformly spread to form the enteric coating layer; the weight gain of the enteric coating layer is 8 wt %~20 wt %.

10. An andrographolide enteric targeting preparation, characterized in that, the micropellet according to any one of the $1^{st}$~$7^{th}$ paragraphs is prepared into granules or capsules.

11. Use of the andrographolide, the micropellets according to any one of $1^{st}$~$7^{th}$ paragraphs or the targeting preparation of the $10^{th}$ paragraph in preparation of a medicine for treating inflammatory bowel disease (IBD).

12. The use according to the $11^{th}$ paragraph, wherein said IBD is ulcerative colitis (UC) or Crohn's disease.

13. The use according to the $11^{th}$ or $12^{th}$ paragraph, wherein the use includes improving colon adhesion, intestinal wall red swelling and thickening and decreased elasticity.

14. The use according to the $11^{th}$ or $12^{th}$ paragraph, wherein the use includes reducing colon ulcer, hemorrhagic spot and perforation.

15. The use according to any one of the $11^{th}$~$14^{th}$ paragraphs, characterized in that, said medicine is prepared into an enteric preparation.

16. The use according to any one of the $11^{th}$~$14^{th}$ paragraphs, characterized in that, said medicine is prepared into enteric targeting micropellets.

17. The use according to the $16^{th}$ paragraph, characterized in that, said enteric targeting micropellets are prepared into granules or capsules.

DESCRIPTION OF THE DRAWINGS

FIG. 1 indicates the effect of the andrographolide on the body weight of TNBS-caused cotilis mouse.

FIG. 2 is the general observation pictures of the colon in each group in TNBS-caused UC rats (A-F).

FIG. 3 shows the zebra fish intestinal tract in the tested drug group, the Crohn's disease model group and the blank control group (the region surrounded by the green dotted line is the zebra fish intestinal tract).

FIG. 4 indicates the improvement degree of intestinal lumen dilatation in Crohn's disease model after being administrated with the andrographolide at different doses (compared with the blank control group).

FIG. 5 indicates the therapeutical efficacy of andrographolide at different doses in Crohn's disease model calculated on the basis of the intestinal lumen area.

FIG. 6 shows the distribution of neutrophil in the zebra fish intestinal tissue after being treated with the drugs (the region surrounded by the yellow dotted line is the zebra fish intestinal tract and the one represented by the green bright spot is the neutrophil).

FIG. 7 is the cumulative release amount of the drug in the simulated intestinal fluid (phosphate buffer, pH 6.5).

FIG. 8 is the cumulative release amount of the drug in the simulated colonic fluid (phosphate buffer, pH 7.2).

DETAILED DESCRIPTION OF THE INVENTION

In the first aspect of this invention, said IBD chiefly relates to UC and Crohn's disease. By studying, the inventor of the present invention concludes: the andrographolide has an improving effect on colon adhesion, intestinal wall red swelling and thickening and decreased elasticity. In addition, the andrographolide is able to reduce colon ulcer, hemorrhagic spot and perforation.

Said drug of the present invention includes any one qualified drug prepared by using the andrographolide as an active pharmaceutical ingredient (API). Preferably, said drug of the present invention refers to a pharmaceutical composition comprising the andrographolide as the sole API or as one of the APIs.

The andrographolide of the present invention belongs to the prior art, which is either commercially available or prepared by a conventional method. For example, the andrographolide is prepared by the following method: the leaves of *Andrographis paniculata* is soaked in 95% (v/v) ethanol and the resulting ethanol soaking liquid is decolored with activated carbon, and the ethanol in the ethanol soaking liquid is recovered by distillation to give a concentrated liquid. The liquid is allowed to stand still to give coarse crystal. Said coarse crystal is added with 15 times (15×) 95% (v/v) ethanol, dissolved by heating, decolored with activated carbon and filtered while it is hot. The liquid is allowed to stand still to give a light-yellow crystal by recrystallization. The obtained crystal is refined by washing with distilled water, chloroform and methanol to give the final product of andrographolide.

The andrographolide is desirably administrated in a form of pharmaceutical composition. Said composition may be conventionally used in combination with one or more kinds of physiologically acceptable excipients or carriers. If possible, the andrographolide acts as API and administrated directly to patients, preferably the API is administrated directly as a pharmaceutical preparation. In terms of compatibility with other ingredients and safety on the subject, said carriers must be pharmaceutically acceptable.

Said pharmaceutical composition can be prepared into any one of pharmaceutically acceptable dosage forms when applied clinically, including but not limited to: tablets, e.g. sugar-coated tablets, film-coated tablets and enteric-coated tablets; capsules, e.g. hard capsules, soft capsules or enteric capsules; injections; suppositories, e.g. intestinal suppositories; drops etc., preferably enteric preparations, e.g. enteric tablets and enteric capsules.

The pharmaceutically acceptable excipients may be added when preparing said pharmaceutical composition into the pharmaceutical preparations.

As for oral preparations, it may include conventional excipients, e.g. adhesives, filling agents, diluents, tableting agents, lubricants, disintegrating agents, colorant agents, flavoring agents and wetting agents. If necessary, the tablets may be coated. The suitable filling agents include cellulose, mannitol, lactose and other analogous filling agents. The suitable disintegrating agents include starch, polyvinylpyrrolidone (PVP) and starch derivatives (e.g. sodium starch glycolate). The suitable lubricants include magnesium stearate. The suitable wetting agents include sodium dodecyl sulfate. The oral solid preparations can be prepared by a conventional method of blending, filling, tableting etc.

Repeated blending is performed to make the API distributed uniformly in compositions in which a large amount of filling agents is used.

As for injections, said liquid unit preparation contains the andrographolide and aseptic carries. Whether said API is dissolved or suspended in the liquid depends on the type and concentration of the carries. Generally, the solution is prepared by dissolving the API in one kind of the carries, sterilizing, loading into an appropriate vial or ampoule and sealing. Pharmaceutically acceptable adjuvants, e.g. local anesthetics, preservatives and buffering agents can be dissolved into the carries as required. In order to improve its stability, after being loaded into the vial, the pharmaceutical composition of the present invention can be frozen and treated in vacuum to remove water.

The effective daily dose of the medicine for adult treatment is always in the range of 0.02~5000 mg when being used for prevention and treatment of UC and Crohn's disease, preferably 1~1500 mg. Said dose needed for treatment is either a single dose or a multi-dose, at which the medicine is administrated at proper intervals, such as twice, triple, four times or more per day. The preparation of the present invention may include 0.1 wt %~99.9 wt % of the API.

In the second aspect of the present invention, a new pH-dependent enteric targeting preparation is provided, characterized in that, said andrographolide enteric targeting micropellet is composed of a blank pellet core, a drug layer and an enteric coating layer, wherein said drug layer contains the andrographolide, a polymer A dissolved under a condition of pH≥7.0 and an excipient; the ratio of the andrographolide and the polymer A is 1:2~1:0.2 by weight, preferably 1:1.5~1:0.5; a weight gain of the drug layer is 20 wt %~100 wt %, preferably 30 wt %~80 wt %; said enteric coating layer contains the polymer B dissolved under a condition of pH≥5.5 and an excipient; a weight gain of the enteric coating layer is 5 wt %~30 wt %, preferably 8 wt %~20 wt %, most preferably 10 wt %~18 wt %.

Wherein, said polymer A is the copolymer of methacrylic acid and methyl methacrylate, preferably the copolymer of methacrylic acid and methyl methacrylate in a ratio of 1:2; and said polymer B is the copolymer of methacrylic acid and ethyl acrylate, preferably the copolymer of methacrylic acid and ethyl acrylate in a ratio of 1:1.

Preferably, the polymer A is selected from Eudragit S100 purchased from Rohm Inc., Germany, and the polymer B is preferably Eudragit L series polymers, most preferably Eudragit L100-55.

Said excipients contained in the drug layer include plasticizers, anti-sticking agents, pigments, hydrophilic polymers and surfactants. Preferably, the surfactants are selected from sodium dodecyl sulfate (SDS) or Tween-80 with an adding amount of 0~5 wt % of the andrographolide, preferably 1 wt %~3 wt % of the andrographolide.

Said plasticizer is one or more selected from the group consisting of triethyl citrate, dibutyl sebacate, propanediol and PEG, the amount of the plasticizer is 10 wt %~70 wt % of the polymer A, preferably 10 wt %~20 wt % of the polymer A; said anti-sticking agent is talc powder, the amount of the anti-sticking agent is 25 wt %~100 wt % of the polymer A, preferably 30 wt %~50 wt % of the polymer A, or said anti-sticking agent is glyceryl monostearate, the amount of the anti-sticking agent is 2 wt %~20 wt % of the polymer A, preferably 5 wt %~10 wt % of the polymer A.

The diameter of said blank pellet core is 200~600 μm, preferably 300~500 μm, and the amount of the blank pellet core is 10 wt %~70 wt % of the formulation, preferably 20 wt %~60 wt % of the formulation. Said blank pellet core is the conventional pharmaceutical pellet core, preferably the blank sucrose pellet core or microcrystalline cellulose pellet core.

Said ingredients are presented in proportion by weight parts:the blank pellet core:the andrographolide:the polymer A:the plasticizer:the anti-sticking agent:the surfactant=200:(10-100):(10-100):(1-15):(1-30):(0-3).

Preferably, said ingredients are presented in proportion by weight parts:the blank pellet core:the andrographolide:the polymer A:the plasticizer:the anti-sticking agent:the surfactant=200:(15-66):(13-74):(2-13.5):(3-27):(0-1.32).

Most preferably, said ingredients are presented in proportion by weight parts:the blank pellet core:the andrographolide:the polymer A:the plasticizer:the anti-sticking agent:the surfactant=200:(20-50):(30-60):(5-10):(5-20):(0.5-1.2).

Wherein, said excipients contained in the enteric coating layer include plasticizers and anti-sticking agents which are selected as depicted above. The amount of the plasticizer accounts for 15 wt % of the polymer B and the amount of the anti-sticking agent accounts for 30 wt % of the polymer B.

Seven optimized formulations of the blank pellet core and the drug layer are presented as follows:

| Nos. | Blank pellet core (g) | andro-grapholide (g) | Eurdragit S (g) | Plasticizer (g) | anti-sticking agent (g) | Surfactant (g) |
|---|---|---|---|---|---|---|
| 1 | 200 | 50 | 15 | 2.1 | 4.5 | 1.00 |
| 2 | 200 | 66 | 20 | 3 | 6 | 1.32 |
| 3 | 200 | 66 | 22 | 3.3 | 6.6 | 1.32 |
| 4 | 200 | 44 | 13 | 2 | 3 | 0 |
| 5 | 200 | 58 | 18 | 3.6 | 5.4 | 1.16 |
| 6 | 200 | 15.2 | 40 | 6 | 12 | 0.4 |
| 7 | 200 | 52 | 74 | 13.5 | 27 | 1.26 |

The preparation method for preparing the andrographolide enteric targeting micropellet is presented as follows:

(1) Applying the Drug to the Blank Pellet Cores a). dispersing the polymer A into a pharmaceutical organic solvent to allow it dissolve fully by high-speed shearing mechanical stirring to obtain a polymer A solution; adding the plasticizer and the anti-sticking agent into the polymer A solution, and then adding the andrographolide, well stirring to give a polymer A coating solution; keeping the coating solution as an uniform suspension by maintaining mechanical stirring when coating; and b). weighing the blank pellet cores and charging into a fluidized bed; adjusting an air flow to make the blank pellet cores in a well fluidized state; starting a heating device until a temperature of the blank pellet cores material reaches a preset value, and starting a peristaltic pump to make the polymer A coating solution atomized through a spray gun and uniformly dispersed on the surface of said blank pellet cores to obtain drug-loading micropellets;

(2) Preparation of the Enteric Coating Layer a). dispersing the polymer B into a pharmaceutical organic solvent or water to allow it dissolve fully by high-speed shearing mechanical stirring to obtain a polymer B solution; adding the plasticizer and the anti-sticking agent into the polymer B solution, well stirring to give a polymer B coating solution; and b). charging said drug-loading micropellets into a bottom-spray device of the fluidized bed and coating by utilizing a fluidized bed device, and the polymer B coating solution is uniformly spread to form the enteric coating layer; the weight gain of the enteric coating layer is 5 wt %~30 wt %.

Preferably, the preparation method for preparing the andrographolide enteric targeting micropellet is presented as follows:

(1) Applying the Drug to the Blank Pellet Cores a). dispersing the polymer A into the pharmaceutical ethanol to make the content of the polymer A at 5 wt %, fully dissolving the polymer A by high-speed shearing mechanical stirring to obtain the polymer A solution; continuing to stir uniformly, adding an appropriate amount of the plasticizer, the anti-sticking agent and the surfactant of sodium dodecyl sulfate into the polymer A solution and then adding the andrographolide, well stirring to give the polymer A coating solution; keeping the coating solution as an uniform suspension by maintaining mechanical stirring when coating; and b). weighing the blank sucrose pellet cores in a diameter of 200~600 μm and charging into the fluidized bed; adjusting the air flow to make the pellet cores in a well fluidized state; starting a heating device and maintaining the temperature of the blank pellet cores material at 25-35° C., and starting a peristaltic pump until the temperature of the blank pellet cores material reaches a preset value to make the polymer A coating solution atomized through a spray gun and uniformly dispersed on the surface of said blank pellet cores to obtain drug-loading micropellets;

(2) Preparation of the Enteric Coating Layer a). dispersing the polymer B into the pharmaceutical ethanol to allow it dissolve fully by high-speed shearing mechanical stirring; adding the plasticizer and the anti-sticking agent into the polymer B solution, well stirring to give the polymer B coating solution; and b). charging said drug-loading micropellets into a bottom-spray device of the fluidized bed and coating by utilizing a fluidized bed device, and the polymer B coating solution is uniformly spread to form the enteric coating layer; the weight gain of the enteric coating layer is 8 wt %~20 wt %.

Besides, the present invention also relates to an andrographolide enteric targeting preparation and said preparations include capsules or granules prepared from the micropellets obtained by a conventional method.

Advantages

A specific pH-dependent technique has been used in the present invention, namely the joint use of two pH-dependent polymers, to achieve enteric targeting release in the bodies with different colon pH values.

(1) The first type of enteric material, e.g. Eudragit L 100-55, has been used in the enteric coating layer, ensuring that the medicine does not release in the stomach until exposing the drug layer by quick dissolution of the enteric coating layer after reaching the duodenum.

(2) The second type of enteric material (e.g. Eudragit S 100) is used as a skeleton in the drug layer as the middle layer, among which the drug is uniformly distributed. Gradually, the drug is released by dissolution of the enteric coating layer when the micropellet reaches the duodenum. Under a low pH condition, however, the drug is released a little; only when approaching the end of small intestine at a pH close to 7, the drug is released quickly, because Eudragit S 100 in the drug layer has a retarding effect in the low pH condition.

As depicted above, the andrographolide enteric targeting micropellet of the present invention has a three-layer structure, the blank pellet core, the drug layer and the enteric coating layer. The enteric coating layer is kept intact at a pH below 5.5 when the preparation goes into the stomach. After reaching the duodenum, however, the enteric coating layer is dissolved in a relatively short time period to expose the drug layer. Eudragit S 100 in the drug layer plays a dual role of sustained release and enteric dissolution. The andrographolide is uniformly distributed in Eudragit S 100. After reaching the duodenum, the outer layer is dissolved. As soon as exposing to the body fluid, the andrographolide starts to release. Because the pH value at the duodenum is low, the limited amount of Eudragit S 100 is dissolved and a very little amount of the drugs released at a very slow rate. With transferring of the drug to lower half of gastrointestinal tract, the pH value goes up gradually, the dissolution rate of Eudragit S 100 is accelerated and the release rate of the drug gradually increased. As a result, most of the drug is not released until approaching ileum and colon, capable of treating intestinal inflammation.

The diameter of said blank pellet core of the present invention is 200~600% μm, much less than the clinical commonly-used pellet core of micropellet (500~1000 μm). This will be helpful to improve the specific surface area, increase the contact area between the drug and the inflammatory site, and ensure that the andrographolide plays its therapeutic effect on the IBD. The amount of the blank pellet core accounts for about 10 wt %~70 wt % of the formulation.

The Eudragit series polymers are used as a film material for coating the micropellet, and the plasticizers and the anti-sticking agents are added into the formulation. Wherein, the main role of the plasticizer is not only for reducing glass transition temperature and minimum film forming temperature, but also for increasing flexibility of the polymer film. The main role of the anti-sticking agent is for preventing the film from being sticky, causing bonding mutually among the blank pellet cores. The surfactant may be used for increasing the wetting effect on the drug.

The pharmacological effects of the andrographolide and its new preparation are proven by the following experiments.

Pharmacological Research 1 Pharmacological Study of the Andrographolide on TNBS-induced UC 1. Aim The mice IBD model was used to perform a preliminary evaluation of the andrographolide for treating UC and Crohn's disease 2 Materials 2.1 Animals Fifty SPF Balb/c male mice, weighing 18~24 g, were provided from Beijing Weitonglihua Experimental Animals Inc. and Certificate No. SCX (JING) 2011-0012.

2.2 Raising Conditions

Animals were raised in a barrier animal room, 10 mice in each cage, with a temperature at 20~25° C. and a relative humidity at 40~60%, free access to water and food, padding materials was replaced daily.

2.3 Tested Medicine and Reagents

Tested medicine: andrographolide, white dry powder, was provided by Tasly Modern TCM Resource Inc. with a batch No. 20100501, with a yield rate of 98% and a purity of 98%.

Positive control drug: Sulfasalazine tablet was purchased from Shanghai Sanwei Pharmaceutical Inc. with a batch No. 200206C11 and a specification of 250 mg/tablet, 12 tablets× 5.

Reagents: 2,4,6-trinitrobenzenesulfonic acid (TNBS) was purchased from Sigma Inc. with a batch No. 033K5020 and a specification of 5% (w/v), and 10 ml/bottle.

3 Method 3.1 Preparation of Model

5% (w/v) TNBS solution was diluted with double-distilled water and mixed with 50% (v/v) ethanol in equal volume to have 1.5% (w/v) TNBS solution. In the model control group, the mice were anesthetized with 1 wt % pentobarbital solution at a dose of 0.05 ml/10 g body weight. After being anesthetized, the mice were administrated with 1.5% (w/v) TNBS solution at a dose of 0.1 ml/mouse by gently inserting stomach perfusion device to about 3 cm depth via anus and arriving at the colon, and the IBD was induced. In the saline group, the saline was gently injected into the colon at a dose of 0.1 ml/mouse. In the normal control group, 50% (v/v) ethanol was gently injected into the colon at a dose of 0.1 ml mouse.

3.2 Grouping and Administration

After one week adaptive feeding, all animals were randomly divided into 5 groups according to body weight, 10 mice in one group: the normal control group, the model control group, the andrographolide low-dose group (20 mg/kg/d), the andrographolide high-dose group (40 mg/kg/d) and the positive control group (Sulfasalazine group, 300 mg/kg/d). Two hours after making model, the animals in each treating groups were orally administrated twice daily with the andrographolide and once daily in the positive control group. After successive administration for 7 days, the abdomen was opened 24 hours after the last administration to observe adhesion degree between the colon and other organs. The colon was separated and weighed.

3.4 Evaluation Indices

1. Body weight: after making model, body weight was measured every day to observe the change in the animals.

2. Evaluation of inflammation: the abdomen was opened 24 hours after the last administration to observe adhesion degree between the colon and other organs. Every segment of the colon was taken out and weighed to calculate the percentage of the colon weight to body weight, as the colon index. The formula was presented as follows:

Decrease rate of colon specific weight=(colon index of the model control group−colon index of the treatment group)/colon index of the model control group×100%

3. Histopathological examination: a part of the colon was taken to prepare the pathological section, and the standard for score was as follows:

0 score, no inflammatory symptoms;
1 score, low-grade inflammation with no structure change;
2 score, low-grade leukocyte infiltration;
3 score, high-grade leukocyte infiltration, high vascular density, crypt extension, thickened colon wall and superficial ulcer 4 score, high-grade leukocyte infiltrating exceeding to mucous layer, crypt extension, decrease of goblet cell, high vascular density, thickened colon wall and extensive ulcer 3.5 Statistics SPSS11.5 software was used for analysis and the data were expressed as $\bar{x} \pm S$. Variance analysis was used for comparison of significant difference among groups. $P<0.05$ showed a statistically significant difference.

4. Results 4.1 Effect of the Andrographolide on the Body Weight of TNBS-induced UC Mice The body weight index was able to generally reflect the overall health status of mice. Compared with the normal control group, the mouse growth was affected after forming UC by rectal administration of TNBS and the increase in body weight was slow. Being treated with the andrographolide or sulfasalazine, the body weight increased faster than that in the model control group. Data were seen in FIG. 1.

4.2 Effect of the Andrographolide on the Colon Weight, the Colon Indices and the Decrease Rate of Colon Specific Weight After UC was induced by TNBS, the colon weight and colon indices in the model control group were obviously higher than those in the normal control group, illustrating the successful modeling. After 7 days of administration, compared with the model control group, the colon weight in the andrographolide high-dose group and the sulfasalazine group was reduced significantly ($P<0.01$); the colon indices in the andrographolide high-dose group, low-dose group and the sulfasalazine group were reduced significantly ($P<0.05$, $P<0.01$) and the decrease rates of the colon specific weight were 33.20%, 58.96% and 47.87%. Data were seen in Table 1.

TABLE 1

Effect of the andrographolide on the colon weight, the colon indices and the decrease rate of colon specific weight in the colitis mice

| | Colon weight (g) | Body weight (g) | Colon indices | Decrease rate of colon specific weight (%) |
|---|---|---|---|---|
| Normal group | 0.17 ± 0.03 | 22.92 ± 1.01 | 0.77 ± 0.10 | — |
| Model control group | 0.55 ± 0.15 | 16.32 ± 1.06 | 3.35 ± 0.88 | — |
| Andrographolide low-dose group | 0.43 ± 0.12 | 19.95 ± 2.05 | 2.24 ± 0.90* | 33.20 |
| Andrographolide high-dose group | 0.29 ± 0.09** | 20.95 ± 1.09 | 1.38 ± 0.46** | 58.96 |
| Sulfasalazine group | 0.33 ± 0.06** | 19.13 ± 0.99 | 1.75 ± 0.43** | 47.87 |

Compared with the model control group:
*$P < 0.05$;
**$P < 0.01$ 4.3 Effect of the Andrographolide on Histopathological Changes of Colon in TNBS-induced Colitis Mice After UC was induced by TNBS, a series of symptoms occurred: colon adhesion, intestinal wall red swelling and thickening, decreased elasticity, UC surface, colon hemorrhagic spot and perforation, indicating extensive inflammatory injuries in colon. The intestinal elasticity in the andrographolide groups and the sulfasalazine group was higher than that in the model control group, and the increase of the colon weight was much less than that in the model control group, indicating that the inflammatory reaction such as colon adhesion and inflammatory exudation was weaker than that in the model control group. Histopathological injuries of intestinal mucosa and wall caused by ulcer and hemorrhage etc. were examined with naked eyes; the colon histopathological injuries in the andrographolide high-dose group and the positive control group (Sulfasalazine group) were much lower than that in the model control group. Data were seen in Table 2.

TABLE 2

Effect of andrographolide on the colon score in TNBS-induced colitis mice

|  | Colon scores |
| --- | --- |
| Normal group | 1 |
| Model control group | 3.7 |
| Andrographolide low-dose group | 3.2 |
| Andrographolide high-dose group | 1.8** |
| Sulfasalazine group | 2.8* |

Compared with the model control group:
*P < 0.05;
**P < 0.01

5 Conclusions

There were a lot of methods to make animal colitis model, TNBS/ethanol induced model was the most similar with the UC pathological changes in clinic. Ethanol destroys intestinal mucosal barriers, and TNBS, as a hapten, would make T lymphocytes sensitized by combining with tissue proteins to cause the intestinal inflammation after inducing autoimmune reaction. The model rats caused by this method have lots of similarities with clinical symptoms of US patients: the stool change and intestinal general morphological and histological change.

In this study, the colitis model mice were used to preliminarily evaluate the treating effect of andrographolide. As shown in the results, the high-dose andrographolide (40 mg/kg/d) was able to delay the descending trend of body weight in the mice of the model control group, which, compared with the model control group, could significantly reduce the colon indices (P<0.01), ameliorate colon pathological changes, and the decrease rate of colon specific weight was 58.96%. Considering aforesaid indices, the andrographolide had a significantly improving effect on the colitis in mice, having a certain therapeutical effect on UC and also capable of treating Crohn's disease.

Pharmacological Research 2 Study on Therapeutical Effect of Andrographolide on Dextran Sulfate Sodium (DSS)-induced UC 1. Aim Efficacy of andrographolide on DSS-induced UC was evaluated.

2. Animals

Eighty-four Balb/c mice, SPF grade, half male and half female, weighing 18~22 g, were provided from Guangdong Medical Experimental Animal Center and Certificate number SYXK(YUE) 2008-0002. Raising conditions: 7 mice per cage raised in a group; temperature and humidity: 20-26° C. and 40-70%. The animals were lighted intermittently (10 h days and 14 h nights). The condition of raising room was always remained unchanged, ensuring reliability of experiment results. Animals were fed with the complete pellet feed (provided by Guangdong Medical Experimental Animal Center), free access to food and water via drinking bottle.

3. Main Apparatuses and Reagents 3.1 Main Apparatuses 3.1.1 Electronic balance, accuracy: 0.001 g, Zhongshan Hengxin Electronics Inc.

3.1.2 Auto dehydrating machine for organic tissue (TS-2N, Xiaogan Hongye Medical Device Inc.)

3.1.3 Embedding machine for organic tissue (BM-V II, Xiaogan Hongye Medical Device Inc.)

3.1.4 Machine for paraffin section (RM2135, Leica Inc. Germany)

3.1.5 Machine for spreading and roasting section (CS-V I, Xiaogan Hongye Medical Device Inc.)

3.1.6 Auto staining machine for organic tissue (RS-18 II, Xiaogan Hongye Medical Device Inc.)

3.2 Reagents 3.2.1 Andrographolide was provided by Tasly Modem TCM Resource Inc. with a batch number of 20140508 with a purity>95%;

3.2.2 Positive control drug: mesalazine enteric tablet was purchased from Jiamusi Luling Pharmaceutical Inc., Sunflower Pharmaceutical Group with a batch number of 140225.

3.2.3 dextran sulfate sodium (DSS) was purchased from MPBIO Inc.

4 Dose Designing and Grouping 4.1 Grouping: quarantine-qualified 84 mice were randomly divided into 6 groups: the model control group, the positive control group, the tested drug low-dose intragastric group, the tested drug high-dose intragastric group, the tested drug low-dose intracolonical group and the tested drug high-dose intracolonical group, 14 mice per group. All animals drank 5% DSS solution daily for consecutive 14 days to establish UC model. Animals were administrated with the drug for treatment on the $2^{nd}$ day after being given 5% DSS drinking water.

4.2 Dose: in this study, dose of administration of the mice in all groups was designed on the basis of client's requirements, and the same doses were adopted in both intragastric and intracolonical groups. Animals were not treated in the model control group, the positive control group (mesalazine enteric tablet, 227.5 mg·kg$^{-1}$·d$^{-1}$), the andrographolide low-dose intragastric group (60 mg·kg$^{1}$·d$^{-1}$), the andrographolide high-dose intragastric group (180 mg·kg$^{-1}$·d$^{-1}$), the andrographolide low-dose intracolonical group (60 mg·kg$^{-1}$·d$^{-1}$) and the andrographolide high-dose intracolonical group (180 mg·kg$^{-1}$·d$^{-1}$).

5 Method 5.1 Method of making UC model: all animals drank 5% DSS solution daily for consecutive 14 days.

5.2 Method of administration: on the $2^{nd}$ day after modeling, the mice were treated intragastrically or intracolonically with the drug at 1 mL/100 g once a day for consecutive 14 days.

5.3 Method for sampling in experiment: 2 hours after the last administration, the mice were killed by cervical vertebra dislocation and abdomen was opened to separate the colon. Along mesenteric side, the intestinal lumen was cut and rinsed with 4° C. normal saline and spread on a plastic plate.

5.4 Method for evaluating disease active index (DAI): the disease active index was assessed at the $7^{th}$ and $14^{th}$ day after administration. The method was presented together with the following three parameters: the body weight loss percentages (unchanged BW: 0 score, 1~5: 1 score, 5~10: 2 score, 10~15: 3 score, more than 15: 4 score), stool viscosity (normal stool: 0 score, loosen stool: 2 score, diarrhea: 4 score) and blood stool (normal stool: 0 score, occult blood stool: 2 score and positive blood stool: 4 score). Total score of three parameters was divided by 3 to give the DAI, namely DAI=(BW index score+stool character score+stool blood score)/3.

6 Observation Indices 6.1 Observation: the general clinical symptoms in the mice were observed daily from the beginning to the end of the experiment, and the stool, mental status and death status were recorded.

6.2 Body weight: BW was recorded weekly from the beginning to the end of the experiment.

6.3 Calculation of DAI: DAI was calculated on the $7^{th}$ and $14^{th}$ day after administration so as to assess disease activity.

6.4 The colon mucosal tissue 8~10 cm away from the anus was sampled, embedded with paraffin and stained with routine HE. Colon mucosal injury was observed by a microscope and histological injury was scored based on the following indices: ulcer inflammatory granuloma, fibrosis and pathological degree.

7. Statistics

Data were expressed as mean+standard deviation ($\bar{x}\pm S$). All numerical variables were analyzed with SPSS13.0 software by one-way ANOVA. T-test analysis was used for inter-group comparison. P<0.05 showed a statistically significant difference.

8 Results 7 days after modeling, loosen stool, diarrhea, blood stool and BW loss were observed in the mice of the model control group, while the stool was more shaped in the treatment groups and the occurrence of blood stool was slightly less than that in the model control group. None of the mice was found death during the experiment.

8.1 Effect on the DAI

By comparing disease activity in all groups, diarrhea occurred in the DSS group on the $3^{rd}$~$5^{th}$ days after drinking DSS and the occult blood stool test was positive. On the $5^{th}$~$7^{th}$ days, different levels of blood stool was observed by naked eyes. As such, diarrhea and occult blood stool occurred on the $3^{rd}$~$5^{th}$ days in the positive control group and the andrographolide high-dose intracolonical group, but no obvious naked-eye-observed blood stool was found in the mice after the $5^{th}$ day. 14 days after administration, the number of blood stool and diarrhea in the positive control group and the andrographolide high-dose intracolonical group was less than the model control group and DAI was significantly reduced (P<0.01) in comparison with the model control group, and there was a certain decrease tendency in the number of blood stool and diarrhea in the andrographolide high-dose intragastric group, but having no statistically significant difference in comparison with the model control group. Data were seen in Table 3.

TABLE 3

DAI score in all groups (x ± SD)

| Groups | Dose (mg/kg) | DAI On the $7^{th}$ day | DAI On the $14^{th}$ day |
|---|---|---|---|
| Model control group | | 1.63 ± 0.69 | 2.27 ± 0.91 |
| Positive control group | 227.5 | 1.31 ± 0.14 | 1.10 ± 0.55** |
| Andrographolide low-dose intragastric group | 60 | 1.63 ± 0.99 | 2.01 ± 0.80 |
| Andrographoiide high-dose intragastric group | 180 | 1.43 ± 0.38 | 1.64 ± 0.83 |

TABLE 3-continued

DAI score in all groups (x ± SD)

| Groups | Dose (mg/kg) | DAI On the $7^{th}$ day | DAI On the $14^{th}$ day |
|---|---|---|---|
| Andrographolide low-dose intracolonical group | 60 | 1.67 ± 0.65 | 1.77 ± 0.95 |
| Andrographolide high-dose intracolonical group | 180 | 1.36 ± 0.64 | 1.35 ± 0.18** |

Compared with the model control group:
*P < 0.05,
**P < 0.01

9. Conclusions and Discussions

Up to now, the mechanism of using DSS-induced model has not yet been entirely elucidated. Perhaps, it is associated with many aspects: macrophage dysfunction; intestinal flora imbalance; influence of DNA synthesis of colonic epithelium cell by DSS negative charge; inhibition to epithelial cell proliferation and destroy of intestinal mucosa barrier, which indicated a more ideal model for studying human IBD. As shown in the results, incidence of naked-eye-observed blood stool was reduced just 7 days after administration in the andrographolide high-dose intracolonical group (180 mg/kg), and blood stool and diarrhea were ameliorated 14 days after administration. DAI score was significantly lower than the model control group (P<0.01), which has been proven to have a certain protective effect on UC.

Pharmacological Research 3 Pharmacological Study of Andrographolide on TNBS-induced UC 1. Aim Efficacy of andrographolide on TNBS-induced UC was evaluated.

2 Animals

Eighty-four SD rats, SPF grade, half male and half female, weighing 180-220 g, were provided from Guangdong Medical Experimental Animal Center and Certificate number is SYXK(YUE) 2008-0002. Raising conditions: 5 rats per cage raised in a group; temperature and humidity: 20-26° C. and 40-70%. The animals were lighted intermittently (10 h days and 14 h nights). The condition of raising room was always remained unchanged, ensuring reliability of experiment results. Animals were fed with the complete pellet feed (provided by Guangdong Medical Experimental Animal Center), free access to food and water via drinking bottle.

3. Main apparatuses and reagents 3.1 Main apparatuses 3.1.1 Electronic balance, accuracy: 0.001 g, Zhongshan Hengxin Electronics Inc.

3.1.2 Auto dehydrating machine for organic tissue (TS-12N, Xiaogan Hongye Medical Device Inc.)

3.1.3 Embedding machine for organic tissue (BM-V II, Xiaogan Hongye Medical Device Inc.)

3.1.4 Machine for paraffin section (RM2135, Leica Inc. Germany)

3.1.5 Machine for spreading and roasting section (CS-V I, Xiaogan Hongye Medical Device inc.)

3.1.6 Auto staining machine for organic tissue (RS-18 II, Xiaogan Hongye Medical Device Inc.)

3.2 Reagents 3.2.1 Andrographolide was provided with a batch number of 20140508 with a purity>95%;

3.2.2 Positive control drug: mesalazine enteric tablet was purchased from Jiamusi Luling Pharmaceutical Inc., Sunflower Pharmaceutical Group with a batch number of 140225.

3.2.3 TNBS was purchased from Sigma Inc. with a batch number of SLBG2566V.

4 Dose Designing and Grouping 4.1 Grouping: quarantine-qualified 84 rats were all used for making UC model. The successful rats were randomly divided into 6 groups: the model control group, the positive control group, the andrographolide low-dose intragastric group, the andrographolide high-dose intragastric group, the andrographolide low-dose intracolonical group and the andrographolide high-dose intracolonical group, 14 rats per group.

4.2 Dose: the same doses were adopted in both intragastric and intracolonical groups. Animals were not treated in the model control group, the positive control group (mesalazine enteric tablet, 420 mg·kg$^{-1}$·d$^{-1}$), the andrographolide low-dose intragastric group (30 mg·kg$^{-1}$·d$^{-1}$), the andrographolide high-dose intragastric group (90 mg·kg$^{-1}$·d$^{-1}$), the andrographolide low-dose intracolonical group (30 mg·kg$^{-1}$·d$^{-1}$) and the andrographolide high-dose intracolonical group (90 mg·kg$^{-1}$·d$^{-1}$).

5. Method 5.1 Method of making UC model: the rats were anesthetized. 2 mm-diameter latex tube was gently inserted into the position about 8 cm inside the body of the rats through anus, and TNBS in 50% ethanol solution (TNBS 125 mg/kg) was injected into intestinal lumen with an injector by one time, 0.5 ml/rat. The tail of the rat was lifted up for 30 s to make the model making agent (i.e., TNBS) fully infiltrate into the intestinal lumen of the rats.

5.2 Method of administration: the same dose (1 mL/100 g) was adopted in both intragastric and intracolonical administration, once daily for consecutive 5 days.

5.3 Method for sampling in experiment: 2 hours after the last administration, the rats were killed by cervical vertebra dislocation and abdomen was opened to separate the colon. Along mesenteric side, the intestinal lumen was cut and rinsed with 4° C. normal saline and spread on a plastic plate.

5.4 Scoring method for colon gross morphological injury was referred to scoring method for mucosal injury (Bjelkengren G, Aronsen K F, Augustsson N E, etc. Radioprotective effect of local administration of lysine vasopressin and triglycyl lysine vasopressin on the rectal mucosa in rats[J]. Acta Oncol, 1995, 34(4):487-92) to record the mucosal injury score: dotted line blooding and small red spots (<1 mm): 1 score, piece blooding and big red spots (=1 mm): 3 score; and erosion and ulcer: 5 score.

6 Observation Indices 6.1 Observation: the general clinical symptoms in the rats were daily observed from the beginning to the end of the experiment in the rats.

6.2 BW was recorded at the beginning of the experiment and the end of the experiment.

6.3 Colon injury degree was observed with naked eyes to score the colon gross morphological injury, including blood spot, piece blooding and ulcer.

7. Statistics

Data were expressed as mean+standard deviation ($\bar{x}\pm S$). All numerical variables were analyzed with SPSS13.0 software by one-way ANOVA. T-test analysis was used for inter-group comparison. P<0.05 showed a statistically significant difference.

8. Results 8.1 Effect of Andrographolide on General Conditions in the Rats

In the model control group, on the 1$^{st}$ day, formless watery stool occurred in the rats, increased stool frequency and accompanied with mucus on the 2$^{nd}$~3$^{rd}$ days, lasting to the end of administration. In the positive control group (420 mg/kg), on the 1$^{st}$ day, formless watery stool occurred in the rats and most of watery stool symptoms disappeared in the rats on the 5$^{th}$~6$^{th}$ days. In the andrographolide high-dose intragastric and intracolonical groups (90 mg/kg), on the 1$^{st}$ day, formless watery stool occurred in the rats, symptoms disappeared gradually on the 2$^{nd}$~3$^{rd}$ days and totally disappeared on the 4$^{th}$~5$^{th}$ days.

8.2 Effect of Andrographolide on UC

In the model control group, the intestinal wall of the rats got thickened, ruga disappeared and large area of necrosis appeared, extensive mucosal congestion, edma and ulcer seen in many sites. In the positive control group, the intestinal wall was thickened mildly, a part of ruga disappeared and small area of necrosis appeared, mucosal congestion, edma seen in many sites and the ulcer area was reduced compared with that in the model control group (P<0.05). In the andrographolide high-dose intracolonical group (90 mg/kg), symptoms of colon disease in the rats was relieved obviously, no obvious thickened intestinal wall was found, the ruga was normal, no significant mucosal congestion was observed, and edma and very small area of necrosis was visible topically only. The ulcer area was significantly reduced compared with those in the model control group and the positive control group (P<0.01). Compared with the andrographolide high-dose intragastric group, the area was also reduced (P<0.05). Data were seen in Table 4 and FIG. 2.

TABLE 4

Effect of andrographolide on UC in the rats by different administration routes

| Groups | Dose (mg/kg) | Gross morphological injury score | Ulcer ratio (%) |
|---|---|---|---|
| Model control group |  | 8.87 ± 1.71 | 61.87 |
| Positive control group | 420 | 3.16 ± 1.97* | 35.45* |
| Andrographolide low-dose intragastric group | 30 | 6.71 ± 2.57 | 45.69* |
| Andrographolide high-dose intragastric group | 90 | 3.25 ± 1.98* | 29.21** |
| Andrographolide low-dose intracolonical group | 30 | 6.53 ± 2.12 | 38.54* |
| Andrographolide high-dose intracolonical group | 90 | 1.96 ± 1.09** | 17.21** |

Compared with the model control group:
*P < 0.05;
**P < 0.01

9. Conclusions

As a hapten, TNBS was mostly used in combination with ethanol to build model. The mechanism of this model was set forth as follows: mucosal injury was caused by using ethanol, TNBS, acting as hapten, infiltrated into colon tissue to form complete antigen by combining with high polymeric substance such as tissue proteins to cause immune response (mainly Th1 immune response) and then led to inflammation similar with human CD.

As shown in the results, the andrographolide could ameliorate the diarrhea in TNBS-induced UC model of the rats and have a certain effect on improving colon injury and ulcer ratio. Compared with the andrographolide high-dose intragastric group, the andrographolide high-dose intracolonical group had a stronger effect on improving colon injury and ulcer ratio (P<0.05). It was confirmed that the rectally topical administration had a better effect on improving UC than the introgastric administration, thus having a certain advantage of application.

Pharmacological Research 4 Therapeutical Effect on Zebra Fish Crohn's Disease Model 1. Exploration of Concentration for Efficacy Evaluation in Zebra Fish Crohn's Disease Model Fish farm water of wild-type AB strain zebra fish Crohn's disease model (1 L reverse osmosis water was added with 200 mg instant sea salt with a conductivity of 480~510 S/cm, pH value of 6.9~7.2 and hardness of 53.7~71.6 mg/L $CaCO_3$) was added with the andrographolide in the concentrations of 0 μg/mL, 0.1 μg/mL, 1 μg/mL, 10 μg/mL, 100 μg/mL and 500 μg/mL. At each concentration, 30 zebra fishes were treated, during which death number of the zebra fishes was counted daily and the dead fishes were removed in time. After treatment, the death number of the zebra fishes in each group was analyzed statistically to draw the optimum concentration-effect curve by using JMP software and calculate MNLC. By exploring concentration, solubility of the drug in DMSO was about 250 mg/ml and the administration method was dissolving the drug into the fish farm water. It was found that when the concentration≥500 μg/ml, the drug began to precipitate, and no toxicity and death were found in zebra fish. As a result, the following four concentrations were selected for efficacy evaluation in Crohn's disease in this study: 50 μg/mL, 100 μg/mL, 250 μg/mL and 500 μg/mL.

2. Efficacy of Andrographolide in Zebra Fish Crohn's Disease Model

According to the results of aforesaid concentration exploration, there were 4 levels set in treatment group to evaluate the efficacy in zebra fish Crohn's disease model, respectively 50 μg/ml, 100 μg/ml, 250 μg/ml and 500 μg/ml. Meanwhile, the positive control group (prednisolone administration group, prednisolone in fish farm water at 10 μM), blank control group and Crohn's disease model group.

Crohn's disease model (mainly inflammation) was built by using TNBS (2,4,6-trinitrobenzenesulfonic acid), and 30 zebra fishes were randomly divided into each treating group. 48 hours after treating the zebra fishes with the andrographolide (at aforesaid 4 different concentrations), prednisolone (the positive control group) and excipient (the excipient administration group), 10 zebra fishes were randomly taken out in each group to make observations and to take photographs. Image analysis software was used to analyze the pictures. Moreover, the intestinal mucosal thickness, intestinal lumen diameter and intestinal lumen area were observed carefully under a microscope and the intestinal lumen diameter and intestinal lumen area were analyzed quantitatively. Therapeutical efficacy of the tested drug in zebra fish Crohn's disease was calculated in accordance with the intestinal lumen area in each group. The calculation formula was presented as follows:

Therapeutical efficacy (%)=[1−(the administration group−the blank control group)/(the model group−the blank control group)]×100%

Statistically analyzed results were expressed as mean±SE. Variance analysis was used for comparison among many groups, and Dunnett's T test for comparison between two groups. P<0.05 showed a statistically significant difference.

Figure 3:
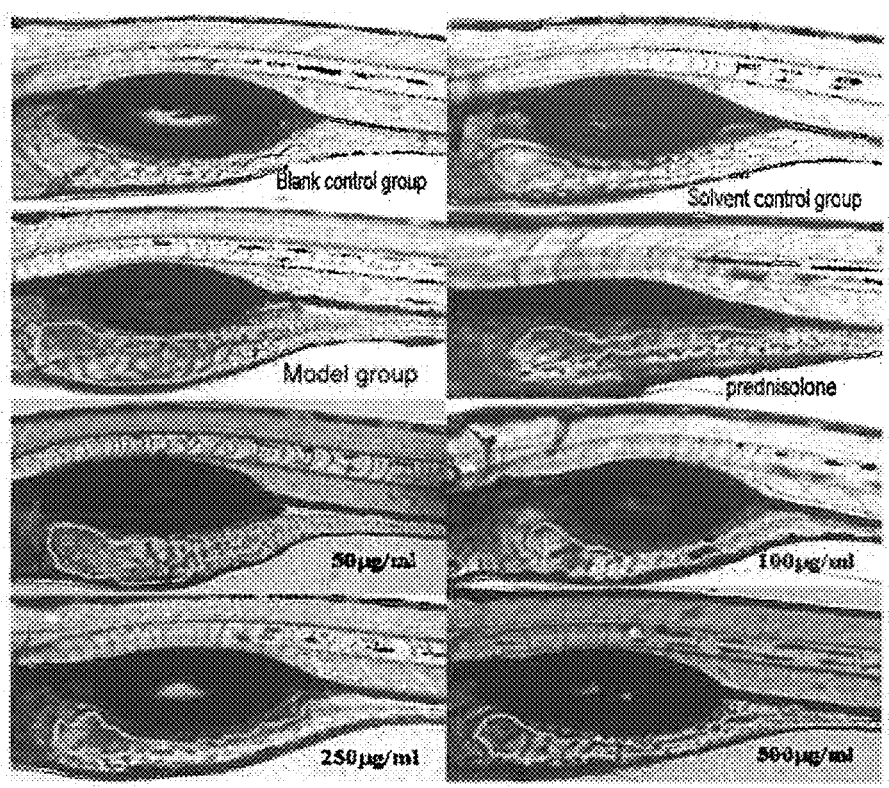

As shown in FIG. 3, in the blank control group and the solvent control group, the intestinal mucosa was smooth, morphologically integrated, intestinal tension obvious and ruga regular. In the model control group (Crohn's disease), zebra fish intestinal lumen was dilated, the intestinal lumen area was increased, the intestinal mucosa thinned and the ruga irregular, flattened or vanished. After the treatment of the positive control drug (prednisolone), Crohn's disease zebra fish intestinal lumen dilation was reduced, the intestinal lumen area was decreased, and the intestinal tension and ruga were recovered significantly. After being treated with low concentration of andrographolide (50 μg/ml), Crohn's disease zebra fish intestinal lumen area was reduced to a certain degree, no obvious recovery of the intestinal tension and ruga was found. High concentrations of andrographolide (100, 250, 500 μg/ml), however, could effectively ameliorate mucosal morphology in colitis, intestinal lumen dilation was reduced significantly, and the intestinal lumen area was close to normal, the intestinal tension and ruga were basically recovered.

Figure 4:
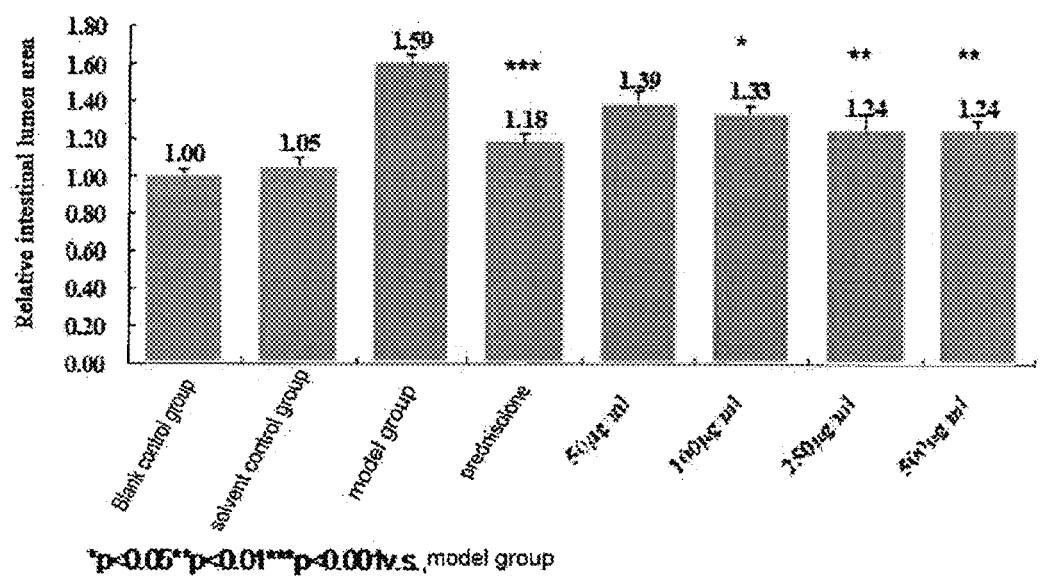
Figure 5:
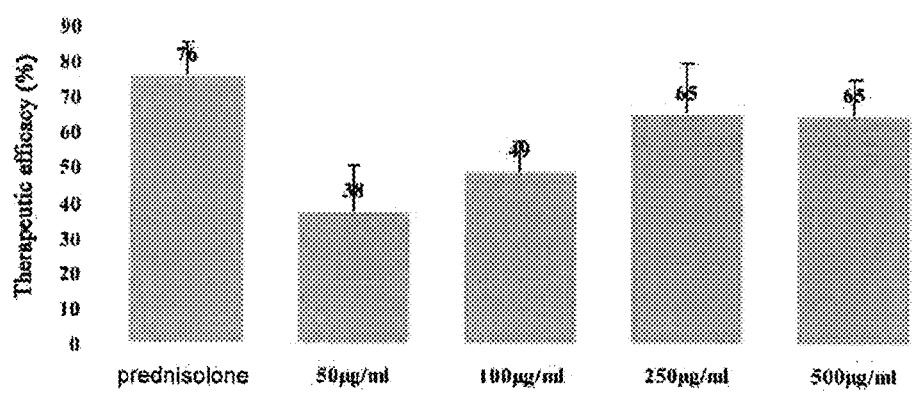

As shown in FIG. 4 and FIG. 5, after being treated with the positive control drug of prednisolone, the intestinal lumen area was reduced by (76±9.3)%, namely the therapeutical efficacy of (76±9.3)%. The andrographolide (50 μg/ml) had a certain therapeutic effect on zebra fish Crohn's disease and the intestinal lumen area was reduced by (38±12.9)%. Compared with the model control group, however, there was no statistically significant difference (P>0.05). In the andrographolide high concentration groups (100, 250 and 500 μg/ml), zebra fish intestinal lumen areas were reduced respectively by (49±8.9)%, (65±14.7)% and (65±10.1)%, having statistically or extremely significant difference (P<0.05 and P<0.01) compared with the model control group.

Figure 6:
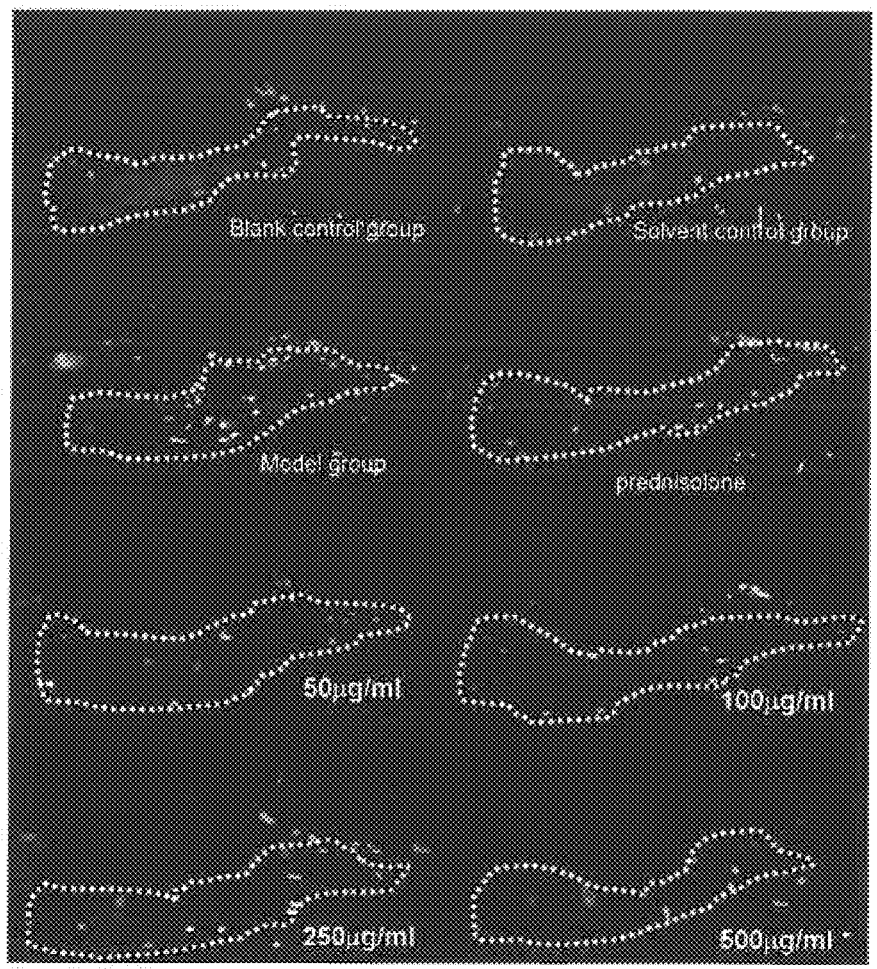

As shown in FIG. 6 and Table 5, a small amount of neutrophil was found in zebra fish intestinal tissue of the blank control group and the solvent control group. In the model control group (Crohn's disease), intestinal lumen was dilated significantly, a large amount of neutrophil was infiltrated in intestinal lumen tissue and inflammation is obvious. The prednisolone of the positive drug could significantly reduce neutrophil in Crohn's disease tissue. Based on the number of neutrophil infiltrated in intestinal lumen, the inflammation regression ratio was (72±4.14)%, having extremely statistically significant difference (p<0.001) compared with the Crohn's disease model group. The andrographolide at different concentrations (50, 100, 250 and 500 μg/ml) could reduce significantly the neutrophil infiltration in intestinal lumen tissue of Crohn's disease zebra fish, facilitate inflammation regression. The inflammation regression ratio in the tissue of Crohn's disease were (45±3.74)%, (46±3.74)%, (63±4.42)% and (79±8.98)%, respectively, having an extremely significant difference (p<0.001) compared with the Crohn's disease model group.

TABLE 5 fluorescence evaluation on neutrophil in Crohn's disease zebra
fish model ($\bar{x} \pm SE$, n = 10)

| Group | Number of Neutrophii | Ratio with the blank control group | Inflammation regression ratio (%) |
|---|---|---|---|
| Blank control group | 9 ± 0.53 | 1.00 ± 0.06 | — |
| Solvent control group | 10 ± 0.27 | 1.07 ± 0.03 | — |
| Model control group | 24 ± 1.17 | 2.70 ± 0.13 | — |
| Positive control group of prednisolone | 14 ± 0.60* | 1.53 ± 0.07* | 72 ± 4.1* |
| Andrographolide (50 µg/ml) | 18 ± 0.54* | 1.97 ± 0.06* | 45 ± 3.7* |
| Andrographolide (100 µg/ml) | 17 ± 0.54* | 1.96 ± 0.06* | 46 ± 3.7* |
| Andrographolide (250 µg/ml) | 15 ± 0.64* | 1.67 ± 0.07* | 63 ± 4.4* |
| Andrographolide (500 µg/ml) | 13 ± 1.30* | 1.40 ± 0.15* | 79 ± 9.0* |

Compared with the model control group,
*$P < 0.001$

Figure 7:
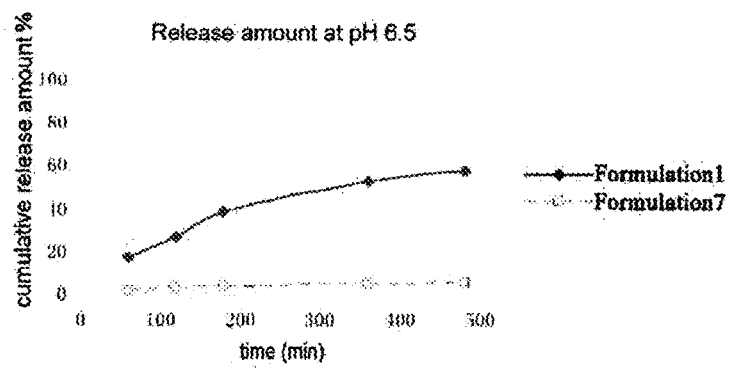
Figure 8:
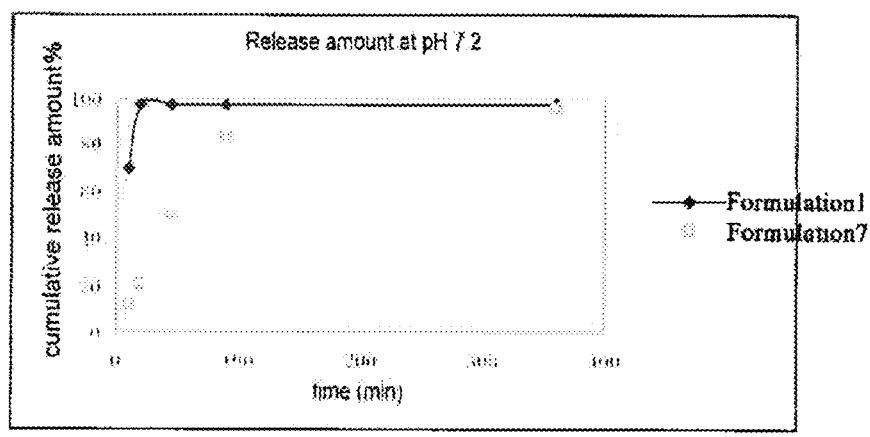

Pharmacological Research 5 Pharmacological Study of pH-dependent Enteric Targeting Preparation In Vitro Release Experiment In vitro release of the micropellets, which were prepared by two formulations selected from aforesaid optimized ones, was determined. That is to say, 150 mg of andrographolide enteric targeting micropellet was loaded into a capsule to measure in vitro release. Dissolution I method of Chinese Pharmacopeia was used at a rotating speed of 100 rpm with different pH salt solutions (1000 ml) as release medium. According to requirement of Chinese Pharmacopeia, after sampling, HPLC was used to measure release amount of the drug during different period of time. The results were seen in FIG. 7 and FIG. 8. Wherein, #1 Formulation had the fastest release rate and #7 Formulations had the slowest release rate. For other formulations, the release rates were the one between the fastest release rate and the slowest release rate.

EXAMPLES

1. Preparative Example for Andrographolide Enteric Tablets and Capsules

Example 1-1

Preparation of Enteric Tablets

Extraction of andrographolide: the leaves of *Andrographis paniculata* was soaked in 95% (v/v) ethanol and the resulting ethanol soaking liquid was decolored with activated carbon and the ethanol is recovered by distillation to give a concentrated liquid. The liquid was allowed to stand still to have coarse crystal. Said coarse crystal was added with 15 times (15×) 95% (v/v) ethanol, dissolved by heating, decolored with activated carbon and filtered while it was hot. The resultant liquid was allowed to stand still to give a light-yellow crystal by recrystallization. The obtained crystal is refined by washing with distilled water, chloroform and methanol to give the final product of andrographolide.

Appropriate amount of excipient was added into the afore-obtained andrographolide to prepare the enteric tablets by a conventional method.

Example 1-2

Preparation of Enteric Capsules

The extracting method was the same as Example 1-1
Appropriate amount of excipient was added into the afore-obtained andrographolide to prepare the enteric capsules by a conventional method. .

Example 1-3

Preparation of Granules

| | |
|---|---|
| andrographolide | 100 g |
| microcrystalline cellulose | 50 g |
| lactose | 50 g |
| starch | 50 g |
| surcose | 250 g |
| to prepare 500 g granules | |

Method:

The extracting method was the same as the Example 1-1. In addition, andrographolide and other excipients in the formulations were screened with 100-mesh sifter, mixed well to prepare into the soft material by using appropriate amount of water, granulated with 14-mesh and sorted out.

Example 1-4

Preparation of Intestinal Suppository

The materials were mixed well according to the formulation of Example 1-3, into which the matrix was added to prepare the intestinal suppository by a conventional method.

2. Examples and Preparative Examples of Andrographolide pH-dependent Enteric Targeting Micropellets It should be noted that the percentage in the following examples and preparative examples refers to the percentage by weight.

Example 2-1

Andrographolide enteric targeting micropellet was composed of a blank pellet core, a drug layer and an enteric coating layer, wherein said drug layer was composed of the following formulation (g):

| Blank pellet core | Andrographolide | Eurdragit S100 | Plasticizer | Anti-sticking agent | Surfactant |
|---|---|---|---|---|---|
| 200 | 50 | 15 | 2.1 | 4.5 | 1.00 |

Wherein, said blank pellet core was a blank sucrose pellet core with a diameter of 600 μm; said plasticizer was triethyl citrate; said anti-sticking agent was talc powder and said surfactant was SDS (sodium dodecyl sulfate);

The enteric coating layer included Eudragit L100-55, plasticizer and anti-sticking agent, and the plasticizer and the anti-sticking agent were selected as depicted in the drug layer. The amount of the plasticizer was 15% of the Eudragit L100-55, the amount of the anti-sticking agent was 30% of the Eudragit L100-55, and the weight gain of coating was 5%.

Example 2-2

Andrographolide enteric targeting micropellet was composed of a blank pellet core, a drug layer and an enteric coating layer, wherein said drug layer was composed of the following formulation (g):

| Blank pellet core | Andrographolide | Eurdragit S100 | Plasticizer | Anti-sticking agent | Surfactant |
|---|---|---|---|---|---|
| 200 | 66 | 20 | 3 | 6 | 1.32 |

Wherein, said blank pellet core was a blank microcrystalline cellulose pellet core with a diameter of 200 μm; said plasticizer was dibutyl sebacate; said anti-sticking agent was glyceryl monostearate and said surfactant was Tween-80;

The enteric coating layer included Eudragit L100-55, plasticizer and anti-sticking agent, and the plasticizer and the anti-sticking agent were selected as depicted in the drug layer. The amount of the plasticizer was 15% of the Eudragit L100-55, the amount of the anti-sticking agent was 30% of the Eudragit L100-55, and the weight gain of coating was 30%.

Example 2-3

Andrographolide enteric targeting micropellet was composed of a blank pellet core, a drug layer and an enteric coating layer, wherein said drug layer was composed of the following formulation (g):

| Blank pellet core | Andrographolide | Eurdragit S100 | Plasticizer | Anti-sticking agent | Surfactant |
|---|---|---|---|---|---|
| 200 | 66 | 22 | 3.3 | 6.6 | 1.32 |

Wherein, said blank pellet core was a blank sucrose pellet core with a diameter of 400 μm; said plasticizer was propanediol; said anti-sticking agent was talc powder and said surfactant was SDS;

The enteric coating layer included Eudragit L100-55, plasticizer and anti-sticking agent, and the plasticizer and the anti-sticking agent were selected as depicted in the drug layer. The amount of the plasticizer was 15% of the Eudragit L100-55, the amount of the anti-sticking agent was 30% of the Eudragit L100-55, and the weight gain of coating was 8%.

Example 2-4

Andrographolide enteric targeting micropellet was composed of a blank pellet core, a drug layer and an enteric coating layer, wherein said drug layer was composed of the following formulation (g):

| Blank pellet core | Andrographolide | Eudragit S 100 | Plasticizer | Anti-sticking agent | Surfactant |
|---|---|---|---|---|---|
| 200 | 44 | 13 | 2 | 3 | 0 |

Wherein, said blank pellet core was a blank sucrose pellet core with a diameter of 500 μm; said plasticizer was propanediol and said anti-sticking agent was talc powder;

The enteric coating layer included Eudragit L30D-55, plasticizer and anti-sticking agent, and the plasticizer and the anti-sticking agent were selected as depicted in the drug layer. The amount of the plasticizer was 15% of the Eudragit L30D-55, the amount of the anti-sticking agent was 30% of the Eudragit L30D-55, and the weight gain of coating was 20%.

Example 2-5

Andrographolide enteric targeting micropellet was composed of a blank pellet core, a drug layer and an enteric coating layer, wherein said drug layer was composed of the following formulation (g):

| Blank pellet core | Andrographolide | Eurdragit S100 | Plasticizer | Anti-sticking agent | Surfactant |
|---|---|---|---|---|---|
| 200 | 58 | 18 | 3.6 | 5.4 | 1.16 |

Wherein, said blank pellet core was a blank sucrose pellet core with a diameter of 500 μm; said plasticizer was PEG and said anti-sticking agent was talc powder;

The enteric coating layer included Eudragit L100-55, plasticizer and anti-sticking agent, and the plasticizer and the anti-sticking agent were selected as depicted in the drug layer. The amount of the plasticizer was 15% of the Eudragit L100-55, the amount of the anti-sticking agent was 30% of the Eudragit L100-55, and the weight gain of coating was 28%.

Example 2-6

Andrographolide enteric targeting micropellet was composed of a blank pellet core, a drug layer and an enteric coating layer, wherein said drug layer was composed of the following formulation (g):

| Blank pellet core | Andrographolide | Eurdragit S100 | Plasticizer | Anti-sticking agent | Surfactant |
|---|---|---|---|---|---|
| 200 | 15.2 | 40 | 6 | 12 | 0.4 |

Wherein, said blank pellet core was a blank sucrose pellet core with a diameter of 500 μm; said plasticizer was PEG and said anti-sticking agent was talc powder;

The enteric coating layer included Eudragit L100-55, plasticizer and anti-sticking agent, and the plasticizer and the anti-sticking agent were selected as depicted in the drug layer. The amount of the plasticizer was 15% of the Eudragit L100-55, the amount of the anti-sticking agent was 30% of the Eudragit L100-55, and the weight gain of coating was 15%.

Example 2-7

Andrographolide enteric targeting micropellet was composed of a blank pellet core, a drug layer and an enteric coating layer, wherein said drug layer was composed of the following formulation (g):

| Blank pellet core | Andrographolide | Eurdragit S100 | Plasticizer | Anti-sticking agent | Surfactant |
|---|---|---|---|---|---|
| 200 | 52 | 74 | 13.5 | 27 | 1.26 |

Wherein, said blank pellet core was a blank sucrose pellet core with a diameter of 500 μm; said plasticizer was triethyl citrate and said anti-sticking agent was talc powder;

The enteric coating layer included Eudragit L100-55, plasticizer and anti-sticking agent, and the plasticizer and the anti-sticking agent were selected as depicted in the drug layer. The amount of the plasticizer was 15% of the Eudragit L100-55, the amount of the anti-sticking agent was 30% of the Eudragit L100-55, and the weight gain of coating was 15%.

Example 2-8

Andrographolide enteric targeting micropellet was composed of a blank pellet core, a drug layer and an enteric coating layer, wherein said drug layer was composed of the following formulation (g):

| Blank pellet core | Andrographolide | Eurdragit S100 | Plasticizer | Anti-sticking agent | Surfactant |
|---|---|---|---|---|---|
| 200 | 66 | 20 | 3 | 6 | 1.32 |

Wherein, said blank pellet core was a blank sucrose pellet core with a diameter of 600 μm; said plasticizer was triethyl citrate; said anti-sticking agent was talc powder and said surfactant was SDS;

The enteric coating layer included Eudragit L100-55, plasticizer and anti-sticking agent, and the plasticizer and the anti-sticking agent were selected as depicted in the drug layer. The amount of the plasticizer was 15% of the Eudragit L100-55, the amount of the anti-sticking agent was 30% of the Eudragit L100-55, and the weight gain of coating was 8%.

Example 2-9

Andrographolide enteric targeting micropellet was composed of a blank pellet core, a drug layer and an enteric coating layer, wherein said drug layer contained the andrographolide, the polymer A dissolved under a condition of pH≥7.0; said ratio of the andrographolide and the polymer A is 1:2 by weight; the weight gain of the drug layer was 20%;

Said enteric coating layer contained the polymer B dissolved under a condition of pH≥5.5 and the weight gain of the enteric coating layer was 8%. The plasticizer and the anti-sticking agent in said enteric coating layer were the same as those in the drug layer, and the proportion between the amount of polymer B and the amount of the plasticizer and the anti-sticking agent in said enteric coating layer was the same as the proportion between the amount of polymer A and the amount of the plasticizer and the anti-sticking agent in the drug layer.

Wherein, said polymer A was the copolymer of methacrylic acid and methyl methacrylate, and said polymer B is the copolymer of methacrylic acid and ethyl acrylate.

Aforesaid plasticizer was triethyl citrate and the anti-sticking agent was talc powder.

Example 2-10

Andrographolide enteric targeting micropellet was composed of a blank pellet core, a drug layer and an enteric coating layer, wherein said drug layer contained the andrographolide, the polymer A dissolved under a condition of pH≥7.0; said ratio of the andrographolide and the polymer A is 1:0.2 by weight; the weight gain of the drug layer was 100%; said enteric coating layer contained the polymer B dissolved under a condition of pH≥5.5 and the weight gain of the enteric coating layer was 20%.

Said polymer A was the copolymer of methacrylic acid and methyl methacrylate in a ratio of 1:2, and the polymer B was the copolymer of methacrylic acid and ethyl acrylate in a ratio of 1:1.

Aforesaid plasticizer was dibutyl sebacate and the anti-sticking agent was glyceryl monostearate.

Example 2-11

Andrographolide enteric targeting micropellet was composed of a blank pellet core, a drug layer and an enteric coating layer, wherein said drug layer contained the andrographolide, the polymer A dissolved under a condition of pH≥7.0; said ratio of the andrographolide and the polymer A is 1:1.5 by weight; the weight gain of the drug layer was 30%; said enteric coating layer contained the polymer B dissolved under a condition of pH≥5.5 and the weight gain of the enteric coating layer was 10%. The plasticizer and the anti-sticking agent in said enteric coating layer were the same as those in the drug layer, and the proportion between the amount of polymer B and the amount of the plasticizer and the anti-sticking agent in said enteric coating layer was the same as the proportion between the amount of polymer A and the amount of the plasticizer and the anti-sticking agent in the drug layer.

Said polymer A was the copolymer of methacrylic acid and methyl methacrylate in a ratio of 1:2, and the polymer B was the copolymer of methacrylic acid and ethyl acrylate in a ratio of 1:1.

Example 2-12

Andrographolide enteric targeting micropellet was composed of a blank pellet core, a drug layer and an enteric coating layer, wherein said drug layer contained the andrographolide, the polymer A dissolved under a condition of pH≥7.0, the plasticizer, the anti-sticking agent, the pigment, the hydrophilic polymer and the surfactant; said ratio of the andrographolide and polymer A is 1:2 by weight; the weight gain of the drug layer was 100%; said plasticizer was selected from triethyl citrate, accounting for 10% of the polymer A; said anti-sticking agent was selected from talc powder, accounting for 25% of the polymer A.

Said enteric coating layer contained the polymer B dissolved under a condition of pH≥5.5 and the weight gain of the enteric coating layer was 20%. The plasticizer and the anti-sticking agent in said enteric coating layer were the same as those in the drug layer, and the proportion between the amount of polymer B and the amount of the plasticizer and the anti-sticking agent in said enteric coating layer was the same as the proportion between the amount of polymer A and the amount of the plasticizer and the anti-sticking agent in the drug layer.

Said polymer A was the copolymer of methacrylic acid and methyl methacrylate in a ratio of 1:2, and the polymer B was the copolymer of methacrylic acid and ethyl acrylate in a ratio of 1:1.

Aforesaid plasticizer was triethyl citrate and the anti-sticking agent was talc powder.

Example 2-13

Andrographolide enteric targeting micropellet was composed of a blank pellet core, a drug layer and an enteric coating layer, wherein said drug layer contained the andrographolide, the polymer A dissolved under a condition of pH≥7.0, the plasticizer and the anti-sticking agent; said ratio of the andrographolide and polymer A is 1:0.5 by weight; the weight gain of the drug layer was 80%; said plasticizer was selected from dibutyl sebacate, accounting for 70% of the polymer A; said anti-sticking agent was selected from talc powder, accounting for 100% of the polymer A.

Said enteric coating layer contained the polymer B dissolved under a condition of pH≥5.5 and the weight gain of the enteric coating layer was 18%. The plasticizer and the anti-sticking agent in said enteric coating layer were the same as those in the drug layer, and the proportion between the amount of polymer B and the amount of the plasticizer and the anti-sticking agent in said enteric coating layer was the same as the proportion between the amount of polymer A and the amount of the plasticizer and the anti-sticking agent in the drug layer.

Said polymer A was the copolymer of methacrylic acid and methyl methacrylate in a ratio of 1:2, and the polymer B was the copolymer of methacrylic acid and ethyl acrylate in a ratio of 1:1.

Example 2-14

Andrographolide enteric targeting micropellet was composed of a blank pellet core, a drug layer and an enteric coating layer, wherein said drug layer contained the andrographolide, the polymer A dissolved under a condition of pH≥7.0, the plasticizer and the anti-sticking agent; said ratio of the andrographolide and the polymer A is 1:1 by weight; the weight gain of the drug layer was 50%; said plasticizer was selected from propanediol, accounting for 20% of the polymer A; said anti-sticking agent was selected from talc powder, accounting for 30% of the polymer A.

Said enteric coating layer contained the polymer B dissolved under a condition of pH≥5.5 and the weight gain of the enteric coating layer was 15%. The plasticizer and the anti-sticking agent in said enteric coating layer were the same as those in the drug layer, and the proportion between the amount of polymer B and the amount of the plasticizer and the anti-sticking agent in said enteric coating layer was the same as the proportion between the amount of polymer A and the amount of the plasticizer and the anti-sticking agent in the drug layer.

Said polymer A was the copolymer of methacrylic acid and methyl methacrylate in a ratio of 1:2, and the polymer B was the copolymer of methacrylic acid and ethyl acrylate in a ratio of 1:1.

Example 2-15

Andrographolide enteric targeting micropellet was composed of a blank pellet core, a drug layer and an enteric coating layer, wherein said drug layer contained the andrographolide, the polymer A dissolved under a condition of pH≥7.0, the plasticizer and the anti-sticking agent; said ratio of the andrographolide and the polymer A is 1:1.5 by weight; the weight gain of the drug layer was 60%; said plasticizer was selected from PEG, accounting for 50% of the polymer A; said anti-sticking agent was selected from talc powder, accounting for 80% of the polymer A.

Said enteric coating layer contained the polymer B dissolved under a condition of pH≥5.5 and the weight gain of the enteric coating layer was 16%. The plasticizer and the anti-sticking agent in said enteric coating layer were the same as those in the drug layer, and the proportion between the amount of polymer B and the amount of the plasticizer and the anti-sticking agent in said enteric coating layer was the same as the proportion between the amount of polymer A and the amount of the plasticizer and the anti-sticking agent in the drug layer.

Said polymer A was the copolymer of methacrylic acid and methyl methacrylate in a ratio of 1:2, and the polymer B was the copolymer of methacrylic acid and ethyl acrylate in a ratio of 1:1.

Example 2-16

Andrographolide enteric targeting micropellct was composed of a blank pellet core, a drug layer and an enteric coating layer, wherein said drug layer contained the andrographolide, the polymer A dissolved under a condition of pH≥7.0, the plasticizer and the anti-sticking agent; said ratio of the andrographolide and the polymer A is 1:1.5 by weight; the weight gain of the drug layer was 60%; said plasticizer was selected from PEG, accounting for 50% of the polymer A; said anti-sticking agent was selected from glyceryl monostearate, accounting for 20% of the polymer A.

Said enteric coating layer contained the polymer B dissolved under condition of pH≥5.5 and the weight gain of the enteric coating layer was 16%. The plasticizer and the anti-sticking agent in said enteric coating layer were the same as those in the drug layer, and the proportion between the amount of polymer B and the amount of the plasticizer and the anti-sticking agent in said enteric coating layer was the same as the proportion between the amount of polymer A and the amount of the plasticizer and the anti-sticking agent in the drug layer.

Said polymer A was the copolymer of methacrylic acid and methyl methacrylate in a ratio of 1:2, and the polymer B was the copolymer of methacrylic acid and ethyl acrylate in a ratio of 1:1.

Example 2-17

Andrographolide enteric targeting micropellet was composed of a blank pellet core, a drug layer and an enteric coating layer, wherein said drug layer contained the andrographolide, the polymer A dissolved under a condition of pH≥7.0, the plasticizer and the anti-sticking agent; said ratio of the andrographolide and polymer A is 1:1.5 by weight; the weight gain of the drug layer was 60%; said plasticizer was selected from PEG, accounting for 50% of the polymer A; said anti-sticking agent was selected from glyceryl monostearate, accounting for 20% of the polymer A.

Said enteric coating layer contained the polymer B dissolved under a condition of pH≥5.5 and the weight gain of the enteric coating layer was 16%. The plasticizer and the anti-sticking agent in said enteric coating layer were the same as those in the drug layer, and the proportion between the amount of polymer B and the amount of the plasticizer and the anti-sticking agent in said enteric coating layer was the same as the proportion between the amount of polymer A and the amount of the plasticizer and the anti-sticking agent in the drug layer.

Said polymer A was the copolymer of methacrylic acid and methyl methacrylate in a ratio of 1:2, and the polymer B was the copolymer of methacrylic acid and ethyl acrylate in a ratio of 1:1.

Micropellets in aforesaid Examples were prepared by the following method.

Preparative Example 2-1

(1) Applying the Drug to the Blank Pellet Cores
a). dispersing the polymer A into a pharmaceutical organic solvent to allow it dissolve fully by high-speed shearing mechanical stirring to obtain a polymer A solution; adding the plasticizer and the anti-sticking agent into the polymer A solution, and then adding the andrographolide, well stirring to give a polymer A coating solution; keeping the coating solution as an uniform suspension by maintaining mechanical stirring when coating; and
b). weighing the blank pellet cores and charging into a fluidized bed; adjusting an air flow to make the blank pellet cores in a well fluidized state; starting a heating device until a temperature of the blank pellet cores material reaches a preset value, and starting a peristaltic pump to make the polymer A coating solution atomized through a spray gun and uniformly dispersed on the surface of said blank pellet cores to obtain drug-loading micropellets;
(2) Preparation of the Enteric Coating Layer
a). dispersing the polymer B into a pharmaceutical organic solvent or water to allow it dissolve fully by high-speed shearing mechanical stirring to obtain a polymer B solution; adding the plasticizer and the anti-sticking agent into the polymer B solution, well stirring to give a polymer B coating solution; and
b). charging said drug-loading micropellets into a bottom-spray device of the fluidized bed and coating by utilizing a fluidized bed device, and the polymer B coating solution is uniformly spread to form the enteric coating layer; the weight gain of the enteric coating layer is 5%.

Preparative Example 2-2

(1) Applying the Drug to the Blank Pellet Cores
a). dispersing the polymer A into a pharmaceutical organic solvent to allow it dissolve fully by high-speed shearing mechanical stirring to obtain a polymer A solution; adding the plasticizer and the anti-sticking agent into the polymer A solution, and then adding the andrographolide, well stirring to give a polymer A coating solution; keeping the coating solution as an uniform suspension by maintaining mechanical stirring when coating; and
b). weighing the blank pellet cores and charging into a fluidized bed; adjusting an air flow to make the blank pellet cores in a well fluidized state; starting a heating device until a temperature of the blank pellet cores material reaches a preset value, and starting a peristaltic pump to make the polymer A coating solution atomized through a spray gun and uniformly dispersed on the surface of said blank pellet cores to obtain drug-loading micropellets;
(2) Preparation of the Enteric Coating Layer
a). dispersing the polymer B into a pharmaceutical organic solvent or water to allow it dissolve fully by high-speed shearing mechanical stirring to obtain a polymer B solution; adding the plasticizer and the anti-sticking agent into the polymer B solution, well stirring to give a polymer B coating solution; and
b). charging said drug-loading micropellets into a bottom-spray device of the fluidized bed and coating by utilizing a fluidized bed device, and the polymer B coating solution is uniformly spread to form the enteric coating layer; the weight gain of the enteric coating layer is 30%.

Preparative Example 2-3

(1) Applying the Drug to the Blank Pellet Cores
a). dispersing the polymer A into the pharmaceutical ethanol to make the content of the polymer A at 5%, fully dissolving the polymer A by high-speed shearing mechanical stirring to obtain the polymer A solution; continuing to stir uniformly, adding an appropriate amount of the plasticizer, the anti-sticking agent and the surfactant of sodium dodecyl sulfate into the polymer A solution and then adding the andrographolide, well stirring to give the polymer A coating solution; keeping the coating solution as an uniform suspension by maintaining mechanical stirring when coating; and
b). weighing the blank sucrose pellet cores in a diameter of 200 μm and charging into the fluidized bed; adjusting the air flow to make the pellet cores in a well fluidized state; starting a heating device and maintaining the temperature of the blank pellet cores material at 25° C., and starting a peristaltic pump until the temperature of the blank pellet cores material reaches a preset value to make the polymer A coating solution atomized through a spray gun and uniformly dispersed on the surface of said blank pellet cores to obtain drug-loading micropellets;
(2) Preparation of the Enteric Coating Layer
a). dispersing the polymer B into the pharmaceutical ethanol to allow it dissolve fully by high-speed shearing mechanical stirring; adding the plasticizer and the anti-sticking agent into the polymer B solution, well stirring to give the polymer B coating solution; and
b). charging said drug-loading micropellets into a bottom-spray device of the fluidized bed and coating by utilizing a fluidized bed device, and the polymer B coating solution is uniformly spread to form the enteric coating layer; the weight gain of the enteric coating layer is 8%.

Preparative Example 2-4

(1) Applying the Drug to the Blank Pellet Cores
a). dispersing the polymer A into the pharmaceutical ethanol to make the content of the polymer A at 5%, fully dissolving the polymer A by high-speed shearing mechanical stirring to obtain the polymer A solution; continuing to stir uniformly, adding an appropriate amount of the plasticizer, the anti-sticking agent and the surfactant of sodium dodecyl sulfate into the polymer A solution and then adding the andrographolide, well stirring to give the polymer A coating solution; keeping the coating solution as an uniform suspension by maintaining mechanical stirring when coating; and
b). weighing the blank sucrose pellet cores in a diameter of 600 μm and charging into the fluidized bed; adjusting the air flow to make the pellet cores in a well fluidized state; starting a heating device and maintaining the temperature of the blank pellet cores material at 35° C., and starting a peristaltic pump until the temperature of the blank pellet cores material reaches a preset value to make the polymer A coating solution atomized through a spray gun and uniformly dispersed on the surface of said blank pellet cores to obtain drug-loading micropellets;

(2) Preparation of the Enteric Coating Layer
a). dispersing the polymer B into the pharmaceutical ethanol to allow it dissolve fully by high-speed shearing mechanical stirring; adding the plasticizer and the anti-sticking agent into the polymer B solution, well stirring to give the polymer B coating solution; and
b). charging said drug-loading micropellets into a bottom-spray device of the fluidized bed and coating by utilizing a fluidized bed device, and the polymer B coating solution is uniformly spread to form the enteric coating layer; the weight gain of the enteric coating layer is 20%.

Preparative Example 2-5

(1) Applying the Drug to the Blank Pellet Cores
a). dispersing the polymer A into the pharmaceutical ethanol to make the content of the polymer A at 5%, fully dissolving the polymer A by high-speed shearing mechanical stirring to obtain the polymer A solution; continuing to stir uniformly, adding an appropriate amount of the plasticizer, the anti-sticking agent and the surfactant of sodium dodecyl sulfate into the polymer A solution and then adding the andrographolide, well stirring to give the polymer A coating solution; keeping the coating solution as an uniform suspension by maintaining mechanical stirring when coating; and
b). weighing the blank sucrose pellet cores in a diameter of 400 μm and charging into the fluidized bed; adjusting the air flow to make the pellet cores in a well fluidized state; starting a heating device and maintaining the temperature of the blank pellet cores material at 32° C., and starting a peristaltic pump until the temperature of the blank pellet cores material reaches a preset value to make the polymer A coating solution atomized through a spray gun and uniformly dispersed on the surface of said blank pellet cores to obtain drug-loading micropellets;

(2) Preparation of the Enteric Coating Layer
a). dispersing the polymer B into the pharmaceutical ethanol to allow it dissolve fully by high-speed shearing mechanical stirring; adding the plasticizer and the anti-sticking agent into the polymer B solution, well stirring to give the polymer B coating solution; and
b). charging said drug-loading micropellets into a bottom-spray device of the fluidized bed and coating by utilizing a fluidized bed device, and the polymer B coating solution is uniformly spread to form the enteric coating layer; the weight gain of the enteric coating layer is 15%.

Preparative Example 2-6

Micropellets obtained from Example 2-1~2-17 were prepared to obtain the conventional granules and capsules.

What is claimed is:

1. An andrographolide enteric targeting micropellet is composed of a blank pellet, a drug layer and an enteric coating layer, wherein said drug layer contains the andrographolide, a polymer A which a copolymer of methacrylic acid and methyl methacrylate in a ratio of 1:2 that dissolves under a condition of pH≥7.0 and an excipient;
   where said ratio of the andrographolide and polymer A is present in a ratio of from about 1:1.5 to about 1:0.5 by weight wherein said ratio provides for the release of a majority of the andrographolide in the distal portion of a human body colon of a sufferer of inflammatory bowel disease; and wherein the weight gain of the drug layer is 20 wt %~100 wt %, said enteric coating layer containing a polymer B which is a copolymer of methacrylic acid and ethyl acrylate in a ratio of 1:1 that dissolves under a condition of pH≥5.5 and an excipient; and
   wherein the weight gain of the enteric coating layer is 5 wt %~30 wt %.

2. The micropellet according to claim 1, wherein the excipient of the drug layer is selected from the group consisting of plasticizer, anti-sticking agent, pigment, hydrophilic polymer and surfactant; and wherein the excipient of the enteric coating layer are selected from the group consisting of plasticizer and anti-sticking agent.

3. The micropellet according to claim 2, wherein the excipients of the drug layer are plasticizer and antisticking agent, wherein the plasticizer is at least one selected from the group consisting of triethyl citrate, dibutyl sebacate, propanediol and polyethylene glycol, and wherein the plasticizer is 10~70 wt % of the polymer A of the drug layer, and wherein said anti-sticking agent is talc, and is 25~100 wt % of the polymer A of the drug layer, or where said anti-sticking agent is glyceryl monostearate, which is 2~20 wt % of the polymer A of the drug layer.

4. The micropellet according to claim 1, wherein the diameter of the blank pellet is 200~600 μm, and wherein the blank pellet is 10~70 wt % of the weight of the micropellet.

5. The micropellet according to claim 2, wherein said ingredients are present in proportion by weight parts: blank micropellet:andrographolide:polymer A:plasticizer:anti-sticking agent:surfactant=200:(10-100):(10-100):(1-15):(1-30):(0-3).

6. A method of preparing the micropellet of claim 1 comprising the following steps:
   (1) applying drug to the blank micropellet by
   a). dispersing the polymer A into a pharmaceutical solvent to allow the polymer A to dissolve in the solvent fully by mechanical stirring to obtain a polymer A solution; adding the excipient into the polymer A solution and then adding the andrographolide to the polymer A solution and then stirring well to provide a polymer A coating solution;

b). weighing the blank micropellet and charging the blank micropellet into a fluidized bed; adjusting the air flow in the fluidized bed to such a degree that the micropellet is well fluidized; starting a heating device and heating the well fluidized blank micropellet until temperature of the well fluidized blank micropellet material reaches a preset value; starting a peristaltic pump to which atomizes the polymer A coating solution through a spray gun to uniformly disperse the polymer A coating solution on the surface of the blank micropellet to obtain a drug-loaded micropellet;

(2) preparing the enteric coating layer by a). dispersing the polymer B into a pharmaceutical solvent to allow the polymer B to dissolve in the solvent fully by mechanical stirring to obtain a polymer B solution; adding the excipient into the polymer B solution and then stirring well to provide a polymer B coating solution;

b). charging aforesaid drug-loaded micropellet into a bottom-spray device of the fluidized bed, and uniformly spreading the polymer B coating solution to form the enteric coating layer; wherein the weight gain of the enteric coating layer is 5 wt %~30 wt %.

7. The preparation method according to claim 6 comprising following steps:

(1) applying drug to the blank micropellet by a). dispersing the polymer A into the pharmaceutical solvent which is ethanol such that the content of polymer A is 5 wt %; fully dissolving the polymer A in the ethanol by mechanical stirring to form the polymer A solution and continuing to uniformly stir the polymer A solution; adding excipient which is plasticizer, anti-sticking agent and the surfactant sodium dodecyl sulfate into the polymer A solution, and then adding the andrographolide to the polymer A solution and then stirring well to provide the polymer A coating solution;

b). weighing the blank micropellet which is a sucrose micropellet having a diameter of 200~600 μm and charging the sucrose micropellet into a fluidized bed; adjusting air flow to such a degree that the sucrose micropellet is well fluidized; starting the heating device and heating the well fluidized sucrose micropellet until the temperature reaches the preset value of 25~35° C., starting the peristaltic pump which atomizes the polymer A coating solution through a spray gun to uniformly disperse the polymer A coating solution on the surface of the sucrose micropellet to obtain a drug-loaded sucrose micropellet;

(2) preparing the enteric coating layer by a). dispersing the polymer B into the pharmaceutical solvent ethanol to allow the polymer B to dissolve in the ethanol fully by high-speed shearing mechanical stirring to obtain a polymer B solution; adding the excipient of the plasticizer and anti-sticking agent into the polymer B solution and stirring well to provide the polymer B coating solution;

b). charging aforesaid drug-loaded sucrose micropellet into a bottom-spray device of the fluidized bed, and uniformly spreading the polymer B coating solution to form the enteric coating layer; wherein the weight gain of the enteric coating layer is 8 wt %~20 wt %.

8. An andrographolide enteric targeting preparation, comprising a capsule or granule prepared from the micropellet of claim 1.

9. A method of preparing medicine for treating inflammatory bowel disease comprising utilizing the micropellet of claim 1.

10. The method of claim 9, wherein said inflammatory bowel disease is ulcerative colitis or Crohn's disease.

11. The method according to claim 9 wherein treating inflammatory bowel disease includes improving colon adhesion, intestinal wall red swelling and thickening and decreased elasticity.

12. The method according to claim 9 wherein treating inflammatory bowel disease includes reducing colon ulcer surface, hemorrhagic spot and perforation.

13. The method of claim 9, wherein the medicine for treating inflammatory bowel disease is an enteric-coated preparation.

14. The method of claim 9, wherein the medicine for treating inflammatory bowel disease is an enteric targeting micropellet.

15. The method of claim 14, characterized in that said enteric targeting micropellet is prepared into a granule or capsule.

16. A method of preparing medicine for treating inflammatory bowel disease comprising utilizing, the targeting preparation of claim 8.

* * * * *